(12) United States Patent
Gill et al.

(10) Patent No.: US 10,287,627 B2
(45) Date of Patent: May 14, 2019

(54) MULTIPLEXED LINKING PCR

(71) Applicant: THE REGENTS OF THE UNIVERSITY OF COLORADO, a body corporate, Denver, CO (US)

(72) Inventors: Ryan T. Gill, Denver, CO (US); Ramsey Zeitoun, Boulder, CO (US); Andrew Garst, Boulder, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 118 days.

(21) Appl. No.: 15/116,300

(22) PCT Filed: Feb. 9, 2015

(86) PCT No.: PCT/US2015/015058
§ 371 (c)(1),
(2) Date: Aug. 3, 2016

(87) PCT Pub. No.: WO2015/120403
PCT Pub. Date: Aug. 13, 2015

(65) Prior Publication Data
US 2017/0009283 A1    Jan. 12, 2017

Related U.S. Application Data

(60) Provisional application No. 61/937,519, filed on Feb. 8, 2014.

(51) Int. Cl.
*C12Q 1/68*       (2018.01)
*C12Q 1/6853*   (2018.01)
*C12P 19/34*     (2006.01)

(52) U.S. Cl.
CPC ............ *C12Q 1/6853* (2013.01); *C12P 19/34* (2013.01); *C12Y 207/07007* (2013.01)

(58) Field of Classification Search
None
See application file for complete search history.

(56) References Cited

U.S. PATENT DOCUMENTS

| | | |
|---|---|---|
| 4,683,202 A | 7/1987 | Mullis |
| 4,965,188 A | 10/1990 | Mullis et al. |
| 5,023,171 A | 6/1991 | Ho et al. |
| 6,204,025 B1 | 3/2001 | Liu |
| 8,467,975 B2 | 6/2013 | Ryan et al. |
| 8,546,136 B2 | 10/2013 | Serber et al. |
| 2007/0141048 A1* | 6/2007 | Oleksiewicz .......... C07K 16/00 424/133.1 |

OTHER PUBLICATIONS

Wetmur et al. (Nucleic Acids Research 2005, 33(8):2615-2619, IDS reference) (Year: 2005).*

(Continued)

*Primary Examiner* — Stephanie K Mummert
(74) *Attorney, Agent, or Firm* — Sheridan Ross P.C.

(57) ABSTRACT

The invention provides compositions and methods for rapid assembly of one or more assembled polynucleotides from a plurality of component polynucleotides, as well as methods of designing polynucleotide primer and linker sets useful in the assembly methods of the invention.

13 Claims, 22 Drawing Sheets

(56) References Cited

OTHER PUBLICATIONS

Chamberlain et al., "Deletion screening of the Duchenne muscular dystrophy locus via multiplex DNA amplification," Oxford Journals, Nucleic Acids Research. 1988, vol. 16(23), pp. 11141-11156.
Eckert et al,, "DNA Polymerase Fidelity and the Polymerase Chain Reaction," PCR methods and Applications, Cold Spring Harbor Laboratory Press, 1991, vol. 1(1), p. 17-24.
Ellis et al., "DNA assembly for synthetic biology: from parts to pathways and beyond," Integrative Biology, 2011, vol. 3(2), pp. 109-118.
Heckman et al., "Gene splicing and mutagenesis by PCR-driven overlap extension," Nature Protocols, 2007, vol. 2(4), pp. 924-932.
Innis, "PCR Protocols: A Guide to Methods and Applications-Optimization of PCRs," Academic Press. Inc., San Diego, CA, 1990, pp. 3-12: 11 pages.
Mattila et al., "Fidelity of DNA synthesis by the Thermococcus litoralis DNA polymerase—an extremely heat stable enzyme with proofreading activity," Oxford University Press, Nucleic Acids Research, 1991, vol. 19(18), pp. 4967-4973.
Saiki, et al. "Enzymatic Amplification of β-Globin Genomic Sequences and Restriction Site Analysis for Diagnosis of Sickle Cell Anemia," Science, 1985, vol. 230, pp. 1350-1352.
Sandoval et al,, "Strategy for directing combinatorial genome engineering in *Escherichia coli*," PNAS Early Edition, 2012, retrieved from www.pnas.org/cgi/doi10.1073/pnas.1206299109, 6 pages.
Wang et al., "Multiplexed Genome Engineering and Genotyping Methods: Applications for Synthetic Biology and Metabolic Engineering," Methods in Enzymology, Chapter Eighteen, 2011, vol. 498, pp. 409-426.
Wang et al., "Programming cells by multiplex genome engineering and accelerated evolution," Nature-Letters, 2009, vol. 460, 14 pages.
Wetmur et al., "Molecular haplotyping by linking emulsion PCR: analysis of paraoxonase 1 haplotypes and phenotypes," Oxford Journals, Nucleic Acids Research, 2005, vol. 33(8), pp. 2615-2619.
Williams et al., "Amplification of complex gene libraries by emulsion PCR," Nature Methods, 2006, vol. 3(7), pp. 545-550.
Williams, "BioTechniques-Synthetic Bio: Expanding PCR's Repertoire | PCR Feature," biotechniques.com, 2012, retrieved from biotechniques.com/news/Synthetic-Bio-Expanding-PCRs-Repertoire/biotechniques-331496.html, 3 pages.

International Search Report and Written Opinion for International (PCT) Patent Application No. PCT/US15/15058, dated Apr. 28, 2015, 8 pages.
U.S. Appl. No. 15/749,540, filed Feb. 1, 2018, Gill et al.
Griffiths et al., "Miniaturising the laboratory in emulsion droplets," Trends in Biotechnology, vol. 24, No. 9, Sep. 2006, pp. 395-402.
Hass, "Mutational Evidence for a Structural Model of the Lassa Virus RNA Polymerase Domain and Identification of Two Residues, Gly1394 and Asp1395, That Are Critical for Transcription but Not Replication of the Genome," Journal of Virology, vol. 82, No. 20, Oct. 2008, pp. 10207-10217.
Kapoor, "Sequencing Human Mitochondrial Hypervariable Region II as a Molecular Fingerprint for Environmental Waters," Environmental Science & Technology, vol. 48, No. 18, 2014, pp. 10648-10655.
Lievre et al., "KRAS Mutation Status Is Predictive of Response to Cetuximab Therapy in Colorectal Cancer," Cancer Research, vol. 66, No. 8, Apr. 2006, pp. 3992-3995.
Paez et al., "EGFR Mutations in Lung Cancer: Correlation with Clinical Response to Gefitinib Therapy," Science, vol. 34, Jun. 2004, pp. 1497-1500.
Porter et al., "Lentiviral and targeted cellular barcoding reveals ongoing clonal dynamics of cell lines in vitro and in vivo," Genome Biology, vol. 15, No. 5, pp. 1-14.
Schorpp et al., "The human ubiquitin C promoter directs high ubiquitous expression of transgenes in mice," Nucleic Acids Research, vol. 24, No. 9, 1996, pp. 1787-1788.
Yarden et al., "The ERBB network: at last, cancer therapy meets systems biology," Nature Reviews Cancer, vol. 12, No. 8, Jul. 2012, pp. 553-563.
Zeitoun et al., "Multiplexed tracking of combinatorial genomic mutations in engineered cell populations," Nature Biotechnology, vol. 33, No. 6, Mar. 23, 2015, pp. 631-637.
International Preliminary Report on Patentability for International (PCT) Patent Application No. PCT/US15/15058, dated Aug. 18, 2016, 7 pages.
International Search Report and Written Opinion for International (PCT) Patent Application No. PCT/US2016/045633, dated Nov. 29, 2016, 6 pages.
International Preliminary Report on Patentability for International (PCT) Patent Application No. PCT/US2016/045633, dated Feb. 15, 2018, 8 pages.

\* cited by examiner

MULTIPLEXED LINKING PCR

CROSS REFERENCE TO RELATED APPLICATION

This application is a national stage application under 35 U.S.C. 371 of PCT Application No. PCT/US2015/015058, having an international filing date of Feb. 9, 2015, which designated the United States, which PCT application claimed the benefit of U.S. Application Ser. No. 61/937,519, filed on Feb. 8, 2014, both of which are incorporated herein by reference in their entirety.

GOVERNMENT INTEREST

This invention was made with Government support under grant number DE-SC0008812 awarded by the U.S. Department of Energy, Office of Science, Office of Biological and Environmental Research, Genomic Science program. The U.S. Government has certain rights in this invention.

TECHNICAL FIELD

The invention relates generally to the field of synthetic biology and, more particularly, to improved methods for the ordered assembly of a plurality of DNA segments into an assembled polynucleotide to assess combinatorial genetic mutation space.

BACKGROUND OF DISCLOSURE

Assessing the effects of combinations of genetic mutations in heterogenous populations of cells (bacteria, eukaryotic etc.) has implications in metabolic and genetic engineering, disease diagnostics and synthetic biology. Particularly, individual genetic mutations conferring a phenotype when found alone, may result novel or unpredictable phenotypes in the presence of other mutations. But current genotyping methods do not adequately assess the effects of combinations of mutations found in heterogenous populations and there are presently no high-resolution and high-throughput techniques for screening combinations of mutations that exist in a population.

Assembly of diverse genetic elements into a single vector traditionally required restriction and ligation enzyme-based methods that are time-consuming and laborious. For example, each sub-cloning step requires the resulting clone be screened and characterized before the introduction of additional fragments. Clones produced by blunt end ligation require confirmation that the fragment was introduced in the proper orientation, while sticky-end ligation requires that the restriction sites utilized to produce the sticky ends on the acceptor fragment also be present in the donor fragment, but not at a site that would interrupt the sequence of interest within the donor fragment. Thus, the selection of workable restriction sites depends entirely on the compositions of the pieces being joined and must be carefully considered in each case. Moreover, the efficiency of such restriction-enzyme based cloning methods is limited by the number of nucleic acid molecules that can be ligated together in a single reaction.

It has been shown that simultaneous amplification of more than one DNA segment can be achieved with a Multiplex polymerase chain reaction (PCR) using primers tagged with unrelated nucleotide sequences which are then ligated together into a single DNA molecule (Chamberlain et al. (1988) Nucleic Acids Research 16 (23): 11141-11156). But PCR products amplified with primers lacking the unrelated nucleotide sequence are not reliably produced due to differences in hybridization kinetics among the primers, and it is therefore necessary to tag each primer with an identical nucleotide sequence to achieve efficient amplification of multiple sequences. All of the PCR products then contain identical unrelated sequences which have to be removed or extended before they could be linked to form one DNA molecule containing all sequences of interest.

One method of amplifying several DNA segments which occur in non-adjacent portions of a DNA sample, termed "splicing by overlap extension" (U.S. Pat. No. 5,023,171), assembles DNA molecules at precise junctions without the use of restriction enzymes or ligase. Component fragments to be recombined are generated in separate polymerase chain reactions using uniquely designed primers which produce amplicons having complementary termini to one another. Upon mixing and denaturation of these amplicons, strands having complementary sequences at their 3' ends overlap and act as primers for each other. Extension of this overlap by DNA polymerase produces a nucleic acid molecule in which the original sequences are spliced together. Subsequent rounds of PCR amplify the resulting spliced polynucleotide. This technique requires time to optimize primer sequences and amplification conditions to produce desired products. Each junction between the fragments to be spliced together must be individually considered, and a pair of primers must be designed for each target DNA fragment in order to make the ends compatible. Considerations for the design of PCR primers, (e.g., melting temperature, G-C content, avoidance of hairpin and dimer formation, and stringency for false priming sites) become increasingly complex as the number of fragments to be spliced in the reaction increases, such that combining more than just three or four target DNA segments becomes an insurmountable PCR reaction design problem. In addition, splicing by overlap extension performs the linker tagging and amplification in each site in a separate reaction, and subsequent reactions are used to assemble the pieces. This limits the usefulness of this technique from a genotyping approach although it is an effective gene construction technique.

Thus, despite advances in recombinant DNA technology, there exists a need for improved methods that provide for the rapid and ordered 1-step assembly of non-adjacent polynucleotides from a heterogenous DNA population. Particularly needed are methods which can facilitate the assembly of a number of polynucleotides with minimal manipulation and characterization of intermediate products, into a single DNA molecule in suitable quantity for accurate characterization of mutations within the assembled DNA fragments and with efficient, high throughput processing that will enable the characterization of multiple mutations that interact to create a specific phenotype. These and other needs can be met by the methods of the present invention.

SUMMARY OF INVENTION

The inventors developed a systematic approach to rapidly and inexpensively genotype combinations of mutations that occur in single genotypes or diverse heterogenous populations. These methods allow for rapid and ordered 1-step assembly of component polynucleotides present in a heterogenous DNA sample into an assembled polynucleotide that can be rapidly and efficiently genotyped. These methods can be used to assemble many types of polynucleotides, including ordered assemblies of mutations from non-adjacent segments of a single genome or from diverse sites present in a sample of combined genomes or genomic fragments, synthetic genes, constructs, cloning vectors, expression vectors, chromosomes, genomes, peptide libraries, and the like.

The basic reaction scheme consists of a two-step PCR process to condense genetic information and create repeating primer-template-primer-linker DNA constructs. In the first PCR reaction, information from a low-concentration template genome is simultaneously amplified and assembled to neighboring sites using a custom random linker sequence. A second PCR reaction selectively amplifies desired constructs. Using these methods, linking N sites together requires a one-pot reaction containing 2N primer species with N−1 linker sequences, resulting in $2N^2+N$ interacting primers that are thermodynamically designed to minimize cross- and self-hybridization. The efficiency of component polynucleotide assembly is hindered by the provision of primer and linker sequences designed to generate a high-density construct (many sites per 1 kb) to allow for sequencing of many sites. These reaction conditions limit primer design, imposing a significant challenge to creating orthogonal and functional primer sets. The complexity of this problem requires an automated and systematic approach to thermodynamic design of primer-linkers that can create high density and numbered constructs.

The linker sequences provide sequence overlap between adjacent component polynucleotides in the assembly reaction. Ideally, the linker sequences lack appreciable secondary structure both at the RNA and at the DNA level, do not cross react in an undesirable manner with one another, and have relatively high melting temperatures.

Thus, in another aspect, the invention provides an automated approach to generate functional and orthoganol primer-linker sets by a process including:
  i) identification of acceptable primers,
  ii) minimization of primer association (such as primer dimers) and,
  iii) selection of random, compatible linker sequences.

An automated software tool was developed to design primers and linkers based on these three steps. To assess the effect of design space, the probability of finding two unassociated primers was quantified as a function of dimensionless design space. It was determined that as design space increased, the probability of finding an unassociated primer pair increased, predictably. As a result, upstream and downstream design space used to design primers will be between 3- and 4-times primer length, or about 100 nt. Optimal linker size was determined to be about 29 nt based on minimizing linker length while maximizing the rate of acceptable linker sequence generation. This modeling approach demonstrates that acceptable primers sets can be found to create information dense constructs of around 100-120 nt, per site linked.

In addition to the thermodynamic primer design, the reaction parameters are also influential. To understand and quantify the kinetics of complex PCR reactions, a scalable microkinetic model was developed to predict PCR products, intermediates, and linking efficiency. One surprising conclusion of this analysis is that the number of amplification cycles to link products asymptotes as the number of sites to link is increased. This results because, although the number of steps to form a final product increases as the number of sites are increased, there are more options and pathways to form final PCR product and this ensures it can form in a single-pot reaction. In addition, the inventors found from the modeling approach that increasing the nucleotide concentration and annealing time and decreasing the primer concentration improved reaction performance.

Thus, one aspect of the invention provides methods of designing primer and linker sets for use in the polynucleotide assembly reactions described above.

In one aspect, the invention provides a method of assembling target sequences within a heterogenous population of nucleic acid molecules comprising: first amplifying a sample of heterogenous nucleic acid molecules containing at least two target sequences in a composition comprising at least two amplification primer pairs, to form a contiguous nucleic acid product molecule comprising each of the at least two target sequences, wherein each of the at least two amplification primer pairs specifically amplifies one of the target sequences; and, wherein at least one amplification primer from each of the at least two amplification primer pairs comprises a linker sequence that is complementary to, and hybridizes with, a linker sequence present on one amplification primer from another one of the at least two amplification primer pairs and amplifying the contiguous nucleic acid product molecule in a composition comprising one amplification primer pair to form multiple copies of the contiguous nucleic acid product molecule.

In this methodology, the amplifying steps may be polymerase chain reaction PCR amplification reactions comprising a DNA polymerase, and deoxyribonucleoside triphosphates (dNTPs). The polymerase may be selected from the group consisting of *Thermus thermophilus* (Tth) DNA polymerase, *Thermus aquaticus* (Taq) DNA polymerase, *Thermotoga neopolitana* (Tne) DNA polymerase, *Thermotoga maritima* (Tma) DNA polymerase, *Thermococcus litoralis* (Tli or VENT™) DNA polymerase, *Pyrococcus furiosus* (Pfu or DEEPVENT™) DNA polymerase, *Pyrococcus woosii* (Pwo) DNA polymerase, *Bacillus sterothermophilus* (Bst) DNA polymerase, *Sulfolobus acidocaldarius* (SAC) DNA polymerase, *Thermoplasma acidophilum* (Tac) DNA polymerase, *Thermus flavus* (Tfl/Tub) DNA polymerase, *Thermus ruber* (Tru) DNA polymerase, *Thermus brockianus* (DYNAZYME™) DNA polymerase, *Methanobacterium thermoautotrophicum* (Mth) DNA polymerase, and mutants, variants, and derivatives thereof.

The amplification step may comprise a 10-fold molar excess of dNTPs. The amplification steps are preferably conducted under conditions suitable for denaturing the nucleic acid molecules, and then annealing of the linker sequence present on one amplification primer to the linker sequence present on one amplification primer from another amplification primer pair.

In one embodiment, the linker sequences are independently at least 24 nucleotides in length. In another embodiment, each of the linker sequences is 29 nucleotides in length. In another embodiment, each of the linker sequences is independently at least 24 nucleotides in length and has a melting temperature of at least 60° C.

In one embodiment, each of the amplification primer sequences is between 18 and 30 nucleotides in length.

In some embodiments, each amplification step is conducted for 35 cycles.

In some embodiments, each amplification step is conducted in a single reaction vessel. In other embodiments, each amplification step is conducted in a separate reaction vessel.

In some embodiments, the contiguous nucleic acid product molecule is sequenced to identify at least one mutation present in a target sequence.

The present invention provides a method of linking by PCR DNA segments which occur in non-adjacent portions of target DNA wherein each DNA segment contains a sequence complementary to a sequence in the DNA segment or segments to which it is to be linked, comprising using a) a first primer which is complementary to the antisense strand of the first DNA segment to be linked and a second primer which is complementary to the sense strand of the last DNA segment to be linked.

In addition, the present invention provides a method of producing and amplifying DNA containing at least three linked DNA segments which occur in non-adjacent portions of target DNA, comprising a) providing a first primer and a second primer for each DNA segment to be amplified, the first primer having a 3' portion which is complementary to the 3' end of the antisense strand of the DNA segment and a 5' tail which is complementary to the 5' end of the second primer for the previous DNA segment or to a sequence internal to the previous DNA segment; the second primer having a 3' portion which is complementary to the 3' end of the sense strand of the DNA segment and a 5' tail which is complementary to the 5' end of the first primer for the subsequent segment or to a sequence internal to the subsequent DNA segment; b) amplifying the at least three DNA segments by multiplex PCR using the pairs of first and second primers; and c) subjecting the at least three amplified DNA segments to a linking PCR using a sense primer which is complementary to the antisense strand of the first segment to be linked and an antisense primer which is complementary to the sense strand of the last segment to be linked.

The present method also provides a methodology for assembling from homogenous cell populations or utilizing an emulsion PCR format to assemble a population in parallel.

This Summary of the Invention is neither intended nor should it be construed as being representative of the full extent and scope of the present invention. Moreover, references made herein to "the present invention," or aspects thereof, should be understood to mean certain embodiments of the present invention and should not necessarily be construed as limiting all embodiments to a particular description. The present invention is set forth in various levels of detail in the Summary of the Invention as well as in the attached drawings and the Description of Embodiments and no limitation as to the scope of the present invention is intended by either the inclusion or non-inclusion of elements, components, etc. in this Summary of the Invention. Additional aspects of the present invention will become more readily apparent from the Description of Embodiments, particularly when taken together with the drawings.

BRIEF DESCRIPTION OF DRAWINGS

FIG. 9 shows the translation of association score versus physical parameters.

DESCRIPTION OF ILLUSTRATIVE EMBODIMENTS

Figure 1:
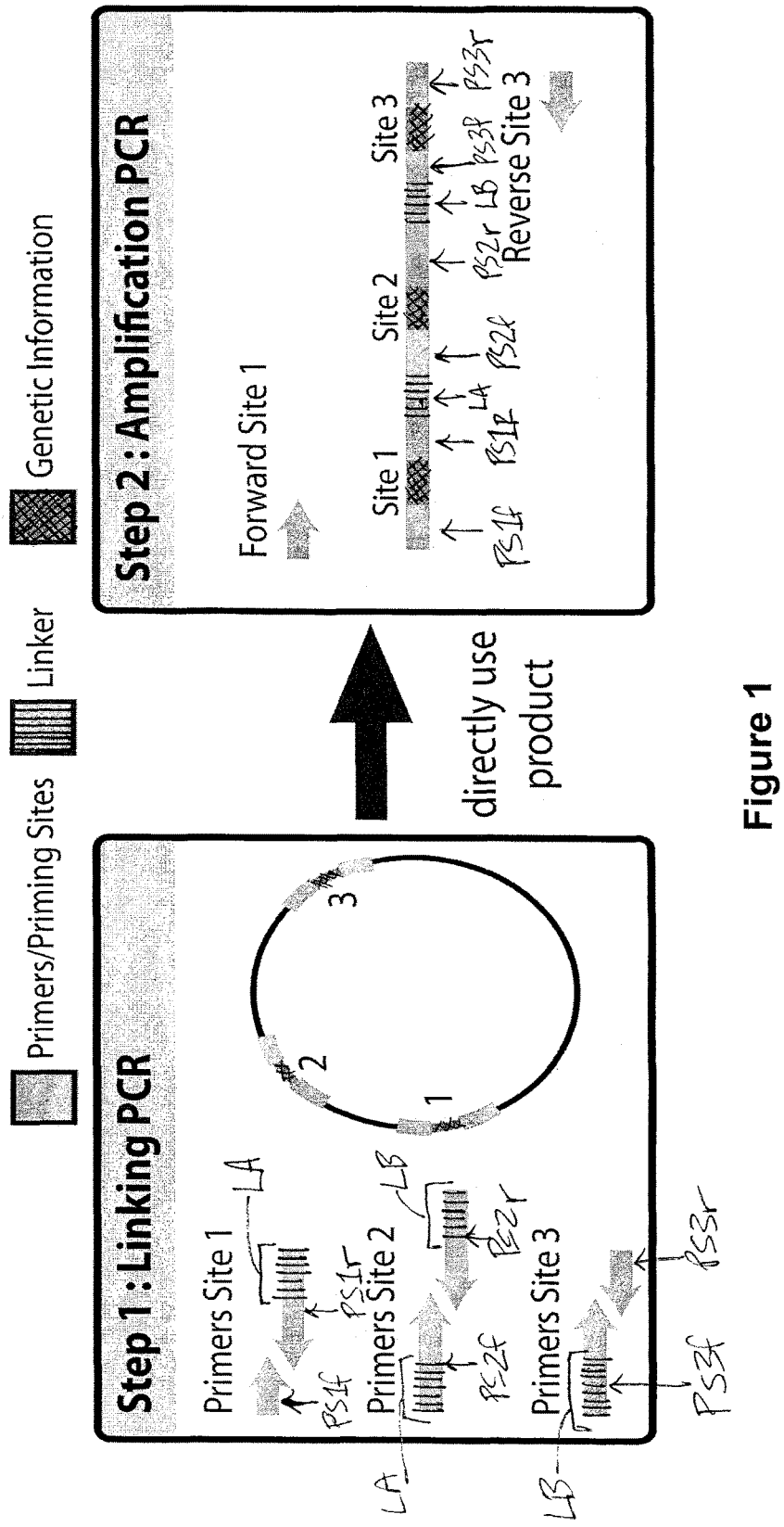
FIG. 1 presents an exemplary method of assembling a single ordered polynucleotide from three, non-adjacent component polynucleotides. A hypothetical genome comprising three DNA segments to be assembled, and primers specific to these three component polynucleotide segments are pooled in a single reaction and subjected to successive rounds of denaturing conditions and annealing conditions sufficient for hybridization of the complementary primer-linker pairs, and primer extension conditions. An assembled polynucleotide comprising the three component polynucleotide segments is produced as a result of the assembling reaction.

The present invention is drawn to rapid, robust, and high-throughput methods for the ordered assembly of a plurality of component polynucleotides into one or more assembled polynucleotides.

In the methods of the invention, linker sequences provide the separate component polynucleotides with complementary termini that are utilized in a splice overlap extension assembly reaction. Combining these reactions assembles the component polynucleotides into an assembled polynucleotide with an ordered sequence, followed by amplification of the assembled polynucleotide useful for subsequent genotyping analysis.

Thus, the methods provide for efficient and rapid assembly of an assembled polynucleotide from a plurality of component polynucleotides. The component polynucleotides may originate from homogenous sources, such as, but not limited to, DNA segments obtained by standard procedures known in the art, such as PCR amplification, chemical synthesis, and the like. Specifically contemplated are target polynucleotide sequences found within genomes from a population of cells and even cells from diverse populations of organisms (e.g., DNA from eukaryotic and prokaryotic organisms). The component polynucleotides may originate from methods used to accelerate evolution in a population, often used in genetic engineering studies (e.g., multiplexed automated genome engineering (MAGE) and Trackable Multiplexed Recombineering (TRMR)).

The methods may be used for assembly into a single assembled polynucleotide of a number of functional DNA elements, including, but not limited to, protein-coding sequences, reporter genes, fluorescent marker coding sequences, promoters, enhancers, terminators, introns, exons, poly-A tails, multiple cloning sites, nuclear localization signals, mRNA stabilization signals, selectable markers, integration loci, epitope tag coding sequences, and degradation signals. The methods can be used for the assembly of any type of assembled polynucleotide, including but not limited to synthetic genes, constructs, cloning vectors, expression vectors, chromosomes, genomic integration constructs, genomes, and DNA libraries.

Furthermore, the methods can be used to assemble the separate component polynucleotides in a single reaction without the need for manipulation and characterization of intermediate products.

Thus, in one aspect, provided herein are methods of assembling a plurality of component polynucleotides into one or more assembled polynucleotides, comprising the steps of:
  a) amplifying a sample of heterogenous nucleic acid molecules containing at least two target sequences in a composition comprising at least two amplification primer pairs, to form a contiguous nucleic acid product molecule comprising each of the at least two target sequences. In this step, each of the at least two amplification primer pairs specifically amplifies one of the target sequences and at least one amplification primer from each of the at least two amplification primer pairs comprises a linker sequence that is complementary to, and hybridizes with, a linker sequence present on one amplification primer from another one of the at least two amplification primer pairs; and,
  b) amplifying the contiguous nucleic acid product molecule in a composition comprising one amplification primer pair to form multiple copies of the contiguous nucleic acid product molecule.

FIG. 1 depicts one embodiment of the assembly methods of the invention for illustrative purposes. In this example, a total of three component polynucleotides are assembled to yield an assembled polynucleotide. However, the assembly methods provided herein can be used to assemble any number of component polynucleotides into one or more assembled polynucleotides. In some embodiments, the methods provided herein result in the assembly of at least two component polynucleotides into one assembled polynucleotide. In some embodiments, the methods provided herein result in the assembly of 2, 3, 4, 6, 8, 9, 10 or more component polynucleotides into one or more assembled polynucleotide.

In the example illustrated in FIG. 1, the DNA composition from which the assembled polynucleotide is generated comprises three sets of PCR primers that specifically amplify each of three separate target sequences (represented as present in non-adjacent positions on a single genome for illustrative purposes in FIG. 1). Thus, Site 1 is specifically amplified by the primers for Site 1 (designated PS1f and PS1 r). Similarly, Site 2 is specifically amplified by the primers for Site 2 (designated PS2f and PS2r), and Site 3 is specifically amplified by the primers for Site 3 (designated PS3f and PS3r).

Additionally, primer PS1 r and PS2f each comprise the linker sequence designated LA, and primer PS2r and PS3f each comprise the linker sequence designated LB.

Assembly of the component polynucleotides into an assembled polynucleotide is enabled by sequence duplexes formed by overlapping strands of complementary termini among the component polynucleotides. Specifically, the linker sequences are designed such that linker sequence LA on PS1 r can hybridize to the complement on PS2f, and linker sequence LB on PS2r can hybridize to the complement on PS3f.

Thus, in the embodiment illustrated in FIG. 1, amplification of the genome containing Site 1, Site 2 and Site 3, in an amplification reaction containing the primers PS1f, PS1r, PS2f, PS2r, PS3f, and PS3r results in the assembly of a single assembled polynucleotide having the sequence:

PS1f-Site 1-PS1r-LA-PS2f-Site 2-PS2r-LB-PS3f-Site 3-PS3r

It should be understood that by careful consideration and ordering of the linker sequences, the polynucleotide sites of interest scattered throughout the genome can be assembled in any order along the single assembled polynucleotide product.

The products of the assembly reaction are then subjected to a limited number of repeating cycles of denaturation/annealing/extension (e.g., for 5-40 cycles) during which a substantial amount of double-stranded copies of the assembled polynucleotide are formed. During this cycling, the component polynucleotides act as both primers and template to generate a full length template for the assembled polynucleotide. As illustrated in FIG. 1, the single assembled polynucleotide is amplified using only the most 5' and most 3' primers (designated PS1f and PS3r in FIG. 1) to produce sufficient copies of the assembled polynucleotide to allow subsequent analysis and characterization of the assembled target sites.

In contrast to the linker sequences LA and LB, the primer segments (PS1f, and PS3r in FIG. 1) are designed to not overlap with each other or any of the linker sequences or DNA segments, but rather serve as binding sites for primers used to amplify the full length assembled polynucleotide. Thus, in step 2 of FIG. 1, primers PS1f and PS2r may be added, and the composition subjected to traditional PCR amplification conditions.

The PCR assembly conditions used are typically 35 cycles. The addition of 100 μM nucleotide triphosphates are added per site linked per reaction. The reaction occurs with an anneal temperature of 60° C. The annealing time used is 30-60 seconds. The PCR amplification conditions can be any PCR amplification conditions deemed suitable by those of skill in the art, including those described in PCR Technology: Principles and Applications for DNA Amplification, ed. H A Erlich, Stockton Press, New York, N.Y. (1989); PCR Protocols: A Guide to Methods and Applications, eds. Innis, Gelfland, Snisky, and White, Academic Press, San Diego, Calif. (1990); Mattila et al. (1991) Nucleic Acids Res. 19: 4967; Eckert, K. A. and Kunkel, T. A. (1991) PCR Methods and Applications 1: 17; and U.S. Pat. Nos. 4,683,202 and 4,965,188, each of which are incorporated herein by reference. In certain embodiments, the PCR step of the amplification reaction comprises 15 to 30 cycles of denaturation, annealing, and extension in the presence of primers complementary to primer binding segments PS1f and PS3r. In certain embodiments, the annealing and extension steps of the PCR can both be performed at 60° C. and 72° C., respectively. However, one of skill in the art will understand that optimal conditions for successful amplification will depend on the thermostable DNA polymerase and the linker sequences utilized, and these conditions may be adjusted accordingly.

Optionally, the assembled polynucleotide can be purified by any technique known to one of skill in the art (e.g., gel electrophoresis purification methods) and used for a variety of purposes, such as analysis of the assembled DNA sites. This analysis may include any well-known DNA analysis, including, for example, RFLP analysis or DNA sequencing. In preferred embodiments, the assembled polynucleotide sites are sequenced using next generation sequencing technologies (such as Illumina's MiSeg™).

The thermostable DNA polymerase used in the assembly reactions to produce the single assembled polynucleotide and in the amplification reactions to amplify the single assembled polynucleotide, may be any thermostable DNA polymerase deemed suitable by those of skill in the art. Thermostable DNA polymerases suitable for use in the present methods include, but are not limited to, *Thermus thermophilus* (Tth) DNA polymerase, *Thermus aquaticus* (Taq) DNA polymerase, *Thermotoga neopolitana* (Tne) DNA polymerase, *Thermotoga maritima* (Tma) DNA polymerase, *Thermococcus litoralis* (Tli or VENT™) DNA polymerase, *Pyrococcus furiosus* (Pfu or DEEPVENT™) DNA polymerase, *Pyrococcus woosii* (Pwo) DNA polymerase, *Bacillus* sterothermophilus (Bst) DNA polymerase, *Sulfolobus acidocaldarius* (SAC) DNA polymerase, *Thermoplasma acidophilum* (Tac) DNA polymerase, *Thermus flavus* (Tfl/Tub) DNA polymerase, *Thermus ruber* (Tru) DNA polymerase, *Thermus* brockianus (DYNAZYME™) DNA polymerase, *Methanobacterium* thermoautotrophicum (Mth) DNA polymerase, and mutants, variants, and derivatives thereof. Thermostable DNA polymerases having high fidelity (i.e., proofreading properties) and low error rates are preferred.

Using this reaction methodology, N sites may be linked together in a one-pot reaction containing 2N primer species with N−1 linker sequences, resulting in $2N^2+N$ interacting primers that must be thermodynamically designed to minimize cross- and self-hybridization. To promote linking, genomic priming site annealing temperatures are selected based on a threshold of 60±0.5° C. while linker temperatures are constrained to 70±0.5° C.

This method results in a high density of desired sites linked versus sequence length. A higher site density enables more sites to be quantified per construct, which is important when long-read sequencing reactions are limited to 1 kb. But the high density constraint limits primer design, imposing an additional challenge to creating an orthogonal and functional primer set. The complexity of this problem requires an automated and systematic approach to thermodynamic design of primer-linkers that can create high density and number constructs.

Thus, another aspect of the invention is an automated method of generating functional primer-linker sets for the PCR assembly reactions described above in the first aspect of the invention. The process includes the three primary steps of:

i) identification of acceptable primers, ii) minimization of primer association (such as primer dimers) and, iii) selection of random linker sequences based on constraints imposed by primer selection and target sequence selection.

An automated software tool, based on these three steps, to design primers-linkers was developed. Random populations of oligomer sequences were modeled to broadly predict the performance of primer design. The probability of finding a randomized sequence that meets standard primer design constraints occurs between 30-50% of a population of oligomers from 18-30 nt. Primers meeting this initial criteria range from 20 and 29 nucleotides (nt) for a melting temperature (Tm)=60±0.5° C. Primer association was scored based on sequence alignment. Higher scores represent a higher number of bases associated, with homologous 20 and 30 nt oligomers having scores of 18±0.6 and 27±1, respectively. It was found that most random oligomers passing basic composition criteria of length 20-30 nt will associate with a threshold score of at least 5 or greater. Primer association in a population was found to be independent and could be predicted as a function of single primer association. These results indicate that a random 20 nt primer should associate with a score of 8 with 95% probability with respect to a pool of 10 primers. To assess the effect of design space, the probability of finding two unassociated primers was quantified as a function of dimensionless design space. It was found that as design space increased, the probability of finding an unassociated primer pair increased, predictably. As a result, upstream and downstream design space used to design primers will be between 3 and 4 times primer length. Optimal linker size was determined to be 29 nt based on minimizing linker length while maximizing the rate of acceptable linker sequence generation. This modeling approach suggests that acceptable primer sets can be found to create information dense constructs. However, kinetic effects are also influential because primers are initially at high concentration with respect to template (~1 µM versus ~1 fM to 1 pM).

To understand and quantify the kinetics of complex PCR reactions, a scalable microkinetic model was developed to predict PCR products and intermediates and predict linking efficiency. One important but unintuitive conclusion of this model was that the number of amplification cycles to link products appears to asymptote as the number of sites to link is increased. This results because, although more sites are linked per construct as sites are increased, there are more options and pathways to form the final product, thereby ensuring it will be possible to create complex constructs using a systematic approach.

Figure 2:
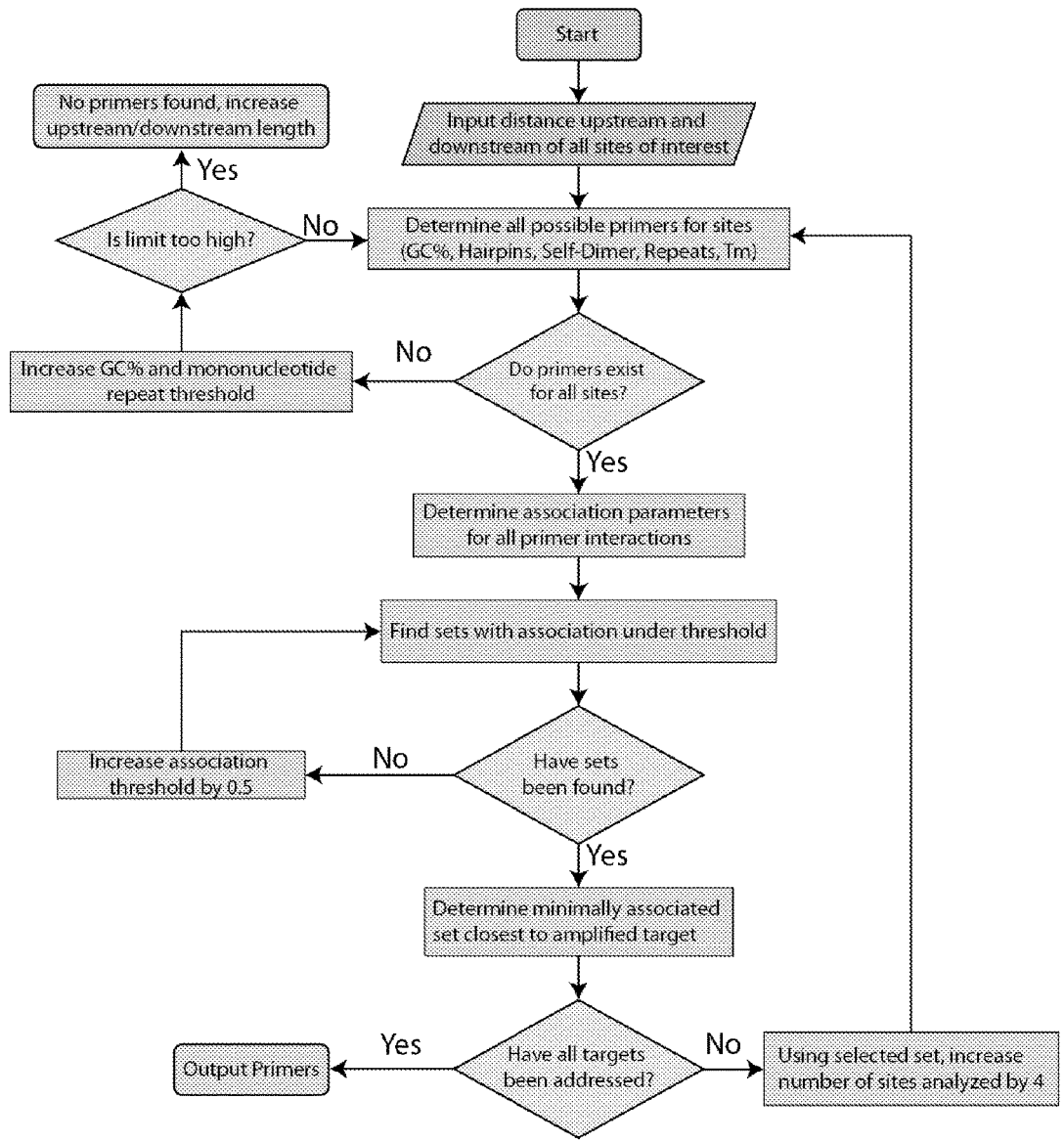
FIG. 2 depicts a flow chart of the primer analysis methodology of the invention that identifies acceptable primers for use in the multiplexed linking PCR methods of the invention.

Within the three-step method described above, the identification of acceptable primers is the first step, and the process is depicted in the flow chart of FIG. 2. The primer design and identification process begins by entering the distance upstream and downstream of each of the polynucleotide sites of interest. All possible primers for these polynucleotide sites of interest, as they exist within the sequence immediately upstream and downstream of each specific site, are generated using methods known to those of skill in the art (including analysis of GC percent content, hairpin structures, self-dimer formations, repeats, and melting temperature). The initial review of the complete sets of primers includes confirming that at least one set of primers exist for each polynucleotide site of interest. If it is determined that there is not at least one set of primers for one or more polynucleotide sites of interest, the stringency criteria for the selection of primers is reduced (i.e., by increasing the GC content or mononucleotide repeat threshold considered acceptable for primer generation) or the length of the potential upstream and downstream region surrounding the polynucleotide site of interest is increased, and the primer generation analysis methodology is run again under these modified conditions. This process is repeated until at least one set of possible primers for each of the polynucleotide sites of interest has been generated.

Thereafter, the complete collection of all possible primers are reviewed and selections are made. Evaluation of complete collection of possible primers begins with a determination of the association parameters for all possible primer interactions of four primers from two sites. All primers from the four regions searched that are minimally associated are chosen. This analysis is continued until by increasing the analysis by four more primers of interest until a complete primer set is identified that has association parameters under the set threshold. If multiple primer sets have been identified and have acceptable association parameters under the set threshold, the minimally associated primer set closest to each polynucleotide site of interest is chosen.

The complete set of primers for all polynucleotide sites of interest to be used in the PCR assembly reactions described above with respect to the first aspect of the invention, are then used in conducting the third step of the automated primer-linker design and identification methods described above: selection of random linker sequences. The linker analysis and design methodology is illustrated by the flowchart depicted in FIG. 3. The sequences of the primers comprising the complete primer sets for each polynucleotide site of interest are evaluated, and a random 29-nucleotide oligomer sequence is generated. Similar to the primer analysis, this random oligomer sequence is evaluated using methods known to those of skill in the art (including analysis of GC percent content, hairpin structures, self-dimer formations, repeats, and melting temperature). If these properties of the random oligomer are not acceptable, a new 29 nucleotide random oligomer is generated and reevaluated until an acceptable oligomer has been identified. When an oligomer meeting the design criteria has been identified, the association of the oligomer with the primers making up the complete primer set is determined. If the randomly generated oligomer is not below the association threshold when evaluated against the complete primer set, a new 29 nucleotide random oligomer is generated, and the evaluation of the random oligomer begins again. However, if the randomly generated oligomer is determined to be below the association threshold when evaluated against the complete primer set, the random oligomer is chosen as a linker sequence and that linker sequence is added to the appropriate primer pairs such that the assembly reactions described above will result in an assembly of individual polynucleotide sites of interest in a specifically desired order to form a single assembled product polynucleotide.

For each of the primer pairs to which the sequence of the linker sequence has been added, the polynucleotides comprising a primer attached to the linker sequence are evaluated using methods known to those of skill in the art (including analysis of GC percent content, hairpin structures, self-dimer formations, repeats, and melting temperature). If these longer linker-primer polynucleotides do not have acceptable properties as PCR primers, a new 29 nucleotide random oligomer is generated, and the evaluation of the random oligomer begins again. Alternatively, if these longer linker-primer polynucleotides do have acceptable properties as PCR primers, then the association of the longer linker-primer polynucleotides with the primers making up the complete primer set is determined. If the longer linker-primer polynucleotides are not below the association threshold when evaluated against the complete primer set, a new 30 nucleotide random oligomer is generated, and the evaluation of the random oligomer begins again. However, if the longer linker-primer polynucleotides are below the association threshold, the design and analysis of additional linkers is continued using the same analysis methodology until the required number of linkers (i.e., N−1 linkers) has been identified. At this point, a complete set of primers and linkers has been designed, analyzed and identified and is ready for use in the assembly reactions described with respect to the first aspect of the invention described above.

Each publication or patent cited herein is incorporated herein by reference in its entirety.

The invention now being generally described will be more readily understood by reference to the following examples, which are included merely for the purposes of illustration of certain aspects of the embodiments of the present invention. The examples are not intended to limit the invention, as one of skill in the art would recognize from the above teachings and the following examples that other techniques and methods can satisfy the claims and can be employed without departing from the scope of the claimed invention.

EXAMPLES

Example 1

The basic reaction scheme of the invention comprises a two-step PCR process to condense genetic information and create repeating primer-template-primer-linker DNA constructs (FIG. 1). In the first PCR reaction, information from a low-concentration template genome is simultaneously amplified and linked to a neighboring site using a custom random linker sequence. A second PCR reaction selectively amplifies desired constructs (FIG. 1). Using this methodology, linking N sites together requires a one-pot reaction containing 2N primer species with N−1 linker sequences, resulting in $2N^2+N$ interacting primers that must be thermodynamically designed to minimize cross- and self-hybridization. The complexity of this problem requires an automated and systematic approach to thermodynamic design of primer-linkers that can create a large number of high density constructs.

Figure 4A:
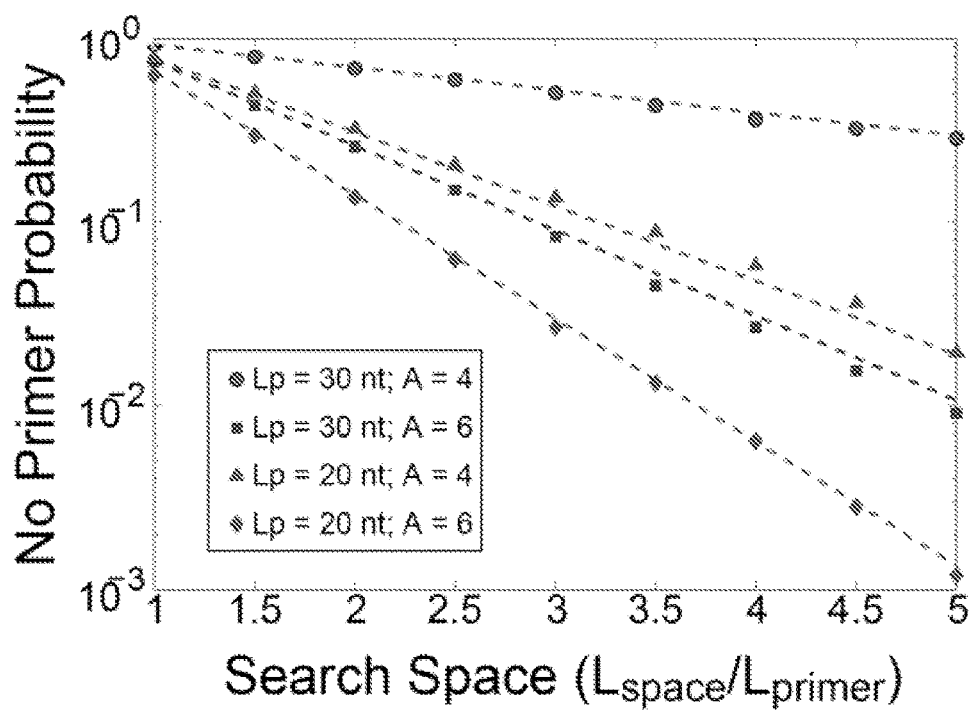
FIG. 4A depicts the automated design of primers and expectations based on minimizing primer-primer interactions while guaranteeing primer fidelity.
Figure 4B:
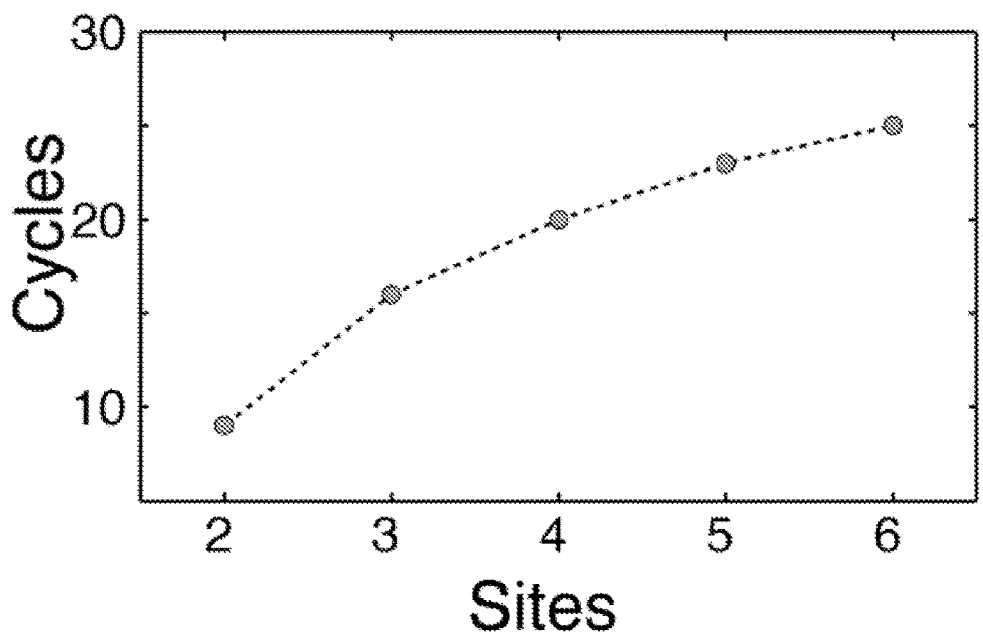
FIG. 4B depicts a kinetic model developed to predict reaction engineering conditions for obtaining final product.
Figure 5:
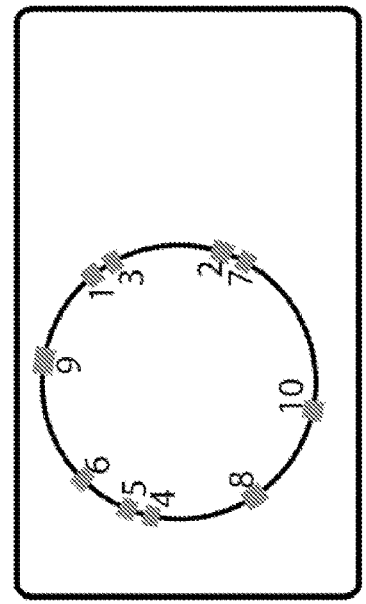
FIG. 5 depicts 10 sites identified on the genome which are subsequently linked together and condensed into a single construct. Gel electrophoresis results of linking 3, 6, 8 and 10 sites by this method are shown.

This example provides a demonstration of these methods. The inventors identified ten-sites across an *E. coli* genome and linked them into a single 10-site construct (FIG. 5). Primers and linkers were designed using the automated methods of the present invention and FIG. 4A shows the expectations based on minimizing primer-primer interactions while guaranteeing primer fidelity. FIG. 4B shows a result from the microkinetic model developed to predict reaction engineering conditions for obtaining the final product.

Figure 6:
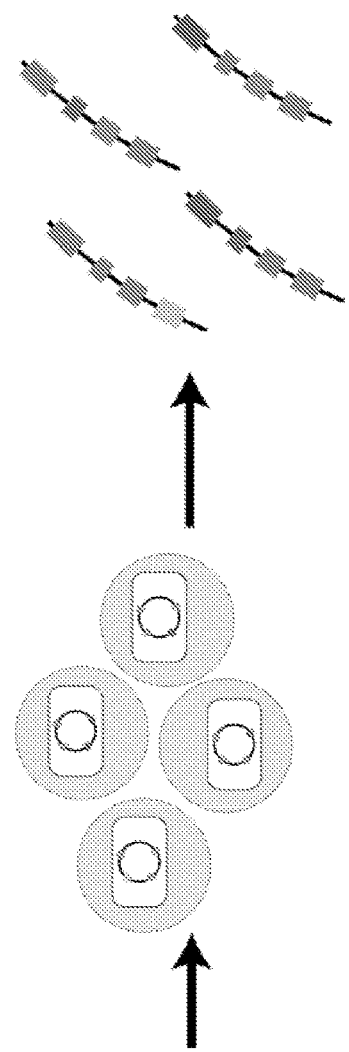
FIG. 6 depicts emulsion PCR used to create population-level constructs to track the combinatorial mutation space.

Additionally, from the same primer pool, 3- 6- and 8-site constructs were linked (FIG. 5, gel lanes 2-5), which accurately gave the genotype present in a single Sanger sequencing read, thereby reducing the Sanger sequencing costs 10-fold. Furthermore, this technique was demonstrated to broadly perform in *E. coli* for separate 9-site, 8-site and 4-site libraries. Finally, to assess heterogeneous populations, the sites in individual cells were linked together in an emulsion PCR for 3- and 4-site constructs (FIG. 6) (Wetmur, et al. (2005) Nucleic Acids Research 33(8):2615-2619, discloses the use an emulsion PCR reaction that can assemble two sites by a different linking process). Emulsion PCR was used to create population-level constructs to track the combinatorial mutation space, and the resulting constructs are only linked to a single cell and a single genotype.

Example 2

Linking PCR can be applied to stitch together PCR products from distal chromosomal origins in a single pot reaction. Not only does this significantly reduce the costs associated with colony based Sanger sequencing by reducing the number of sequencing reactions per clone, but combining this method with emulsification technologies (emulsion PCR (Griffith, Tawfick Trends in Biotechnology 2007)) offers a potentially useful route to multiplexed genotyping of large populations. The limited number of assemblies have limited the effectiveness of other one-pot genotyping methods like emulsion PCR. To be widely applicable as a technology for tracking targeted genomic libraries, such an approach would ideally enable sampling of many genomic sites. To expand the number of gene targets that can be tracked and improve the overall efficiency of this approach requires an automated de novo primer design approach that optimizes the many criteria necessary for efficient PCR based assembly and subsequent analysis. The inventors thus sought to develop an automated approach for optimizing both the primer design and reaction conditions to achieve assembly of a larger number of genomic sites as proof of concept for multiplexed genotyping of distal chromosomal sites of interest.

The basic two-step PCR reaction scheme described above condenses genetic information to create repeating primer-template-primer-linker DNA constructs. In the first PCR reaction, information from a low-concentration template genome is simultaneously amplified and linked to a neighboring site using a custom linker sequence. A second PCR reaction selectively amplifies desired constructs. Linking N sites together requires a one-pot reaction containing 2N primer species with N−1 linker sequences, resulting in $2N^2+N$ interacting primers that must be thermodynamically designed to minimize cross- and self-hybridization.

To promote linking, genomic priming site annealing temperatures were selected based on a threshold of 60±0.5° C. and linker temperatures were constrained for 70±0.5° C. This approach also requires a high density of desired sites linked versus sequence length. A higher site density enables more sites to be quantified per construct, which is important when sequencing read lengths are limited to 1 kb. However, a high density constraint limits primer design space, thereby imposing an additional challenge to creating an orthogonal and functional primer set. The complexity of this problem requires an automated and systematic approach to thermodynamic design of primer-linkers that can create high density and number constructs.

Figure 3:
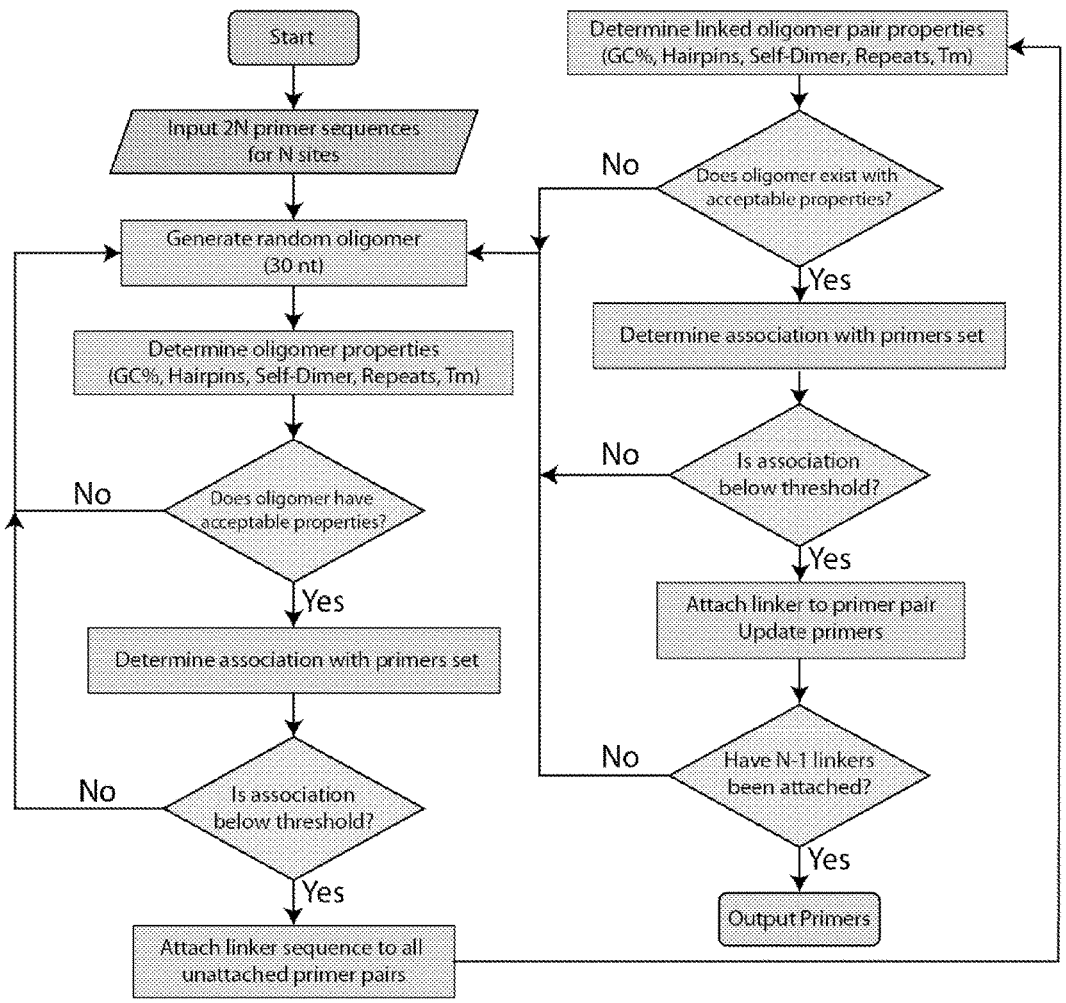
FIG. 3 depicts a flow chart of the linker analysis methodology of the invention that identifies acceptable linker(s) for use in the multiplexed linking PCR methods of the invention.

The inventors developed an automated approach to generate functional primer-linker sets for multiplexed linking PCR that includes a three major step process of:

i) identification of acceptable primers (process depicted in FIG. 2), ii) minimization of primer association (e.g. primer dimers) (process depicted in FIG. 2) and, iii) design of linker sequences (process depicted in FIG. 3).

Figure 7:
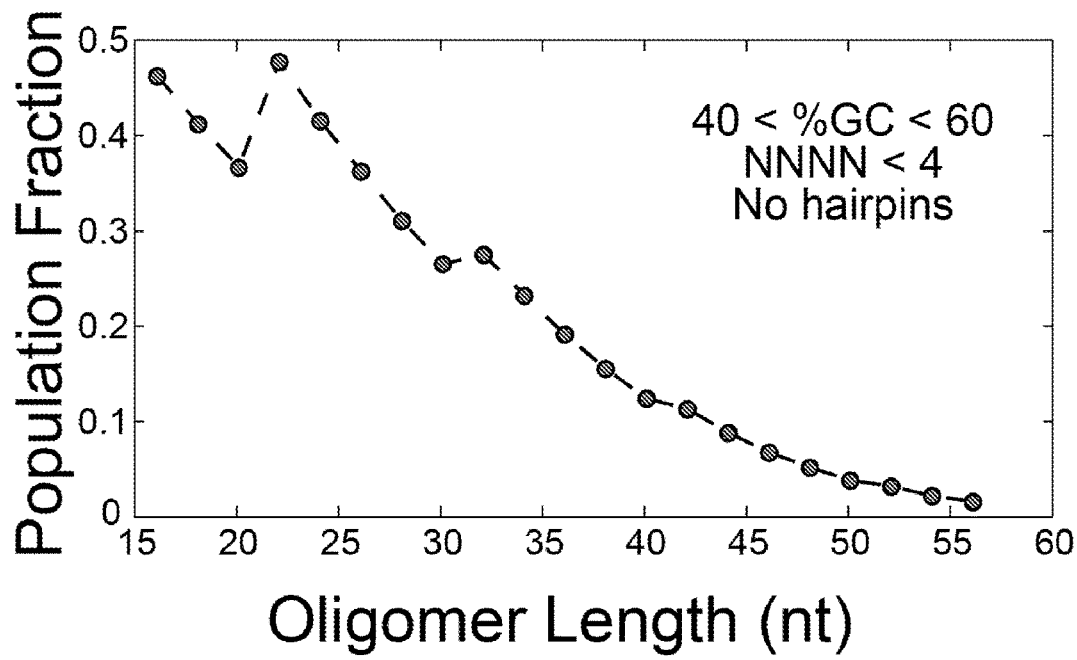
FIG. 7 shows a theoretical calculation of the fraction of random oligomers that satisfy composition and intramolecular thermodynamic properties required for certain embodiments of the present invention.
Figure 8:
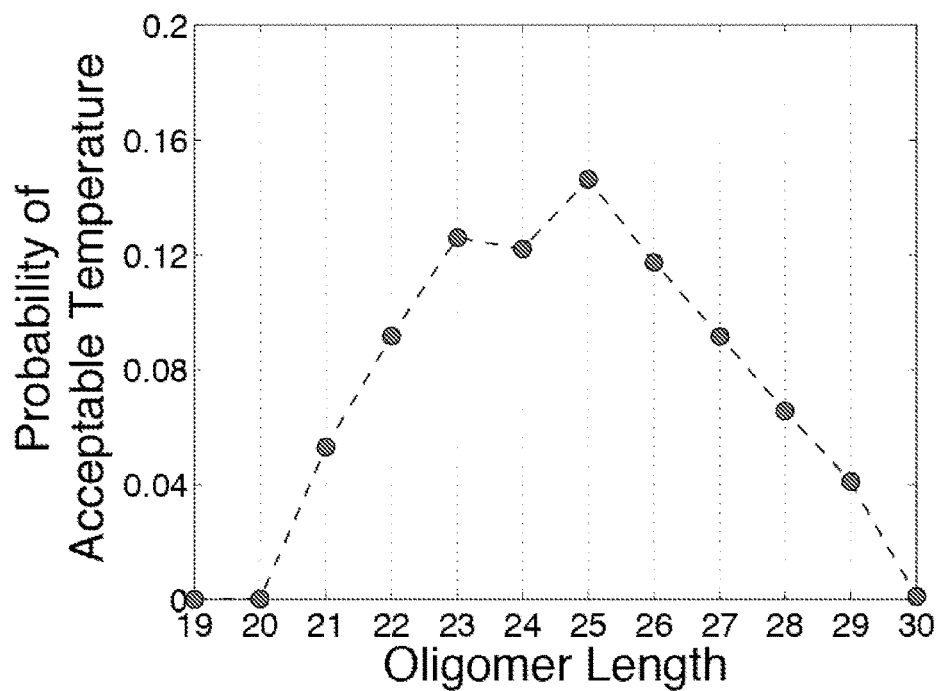
FIG. 8 shows the calculated probability of acceptable oligomers with Tm=60±0.5° C. versus oligomer length.
Figure 9A:
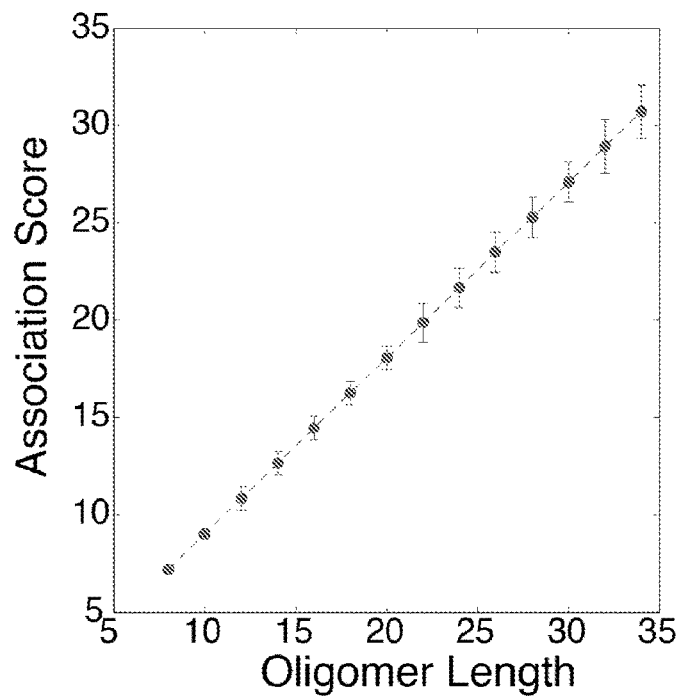
FIG. 9A depicts the linear correlation between association score versus oligomer length.
Figure 9B:
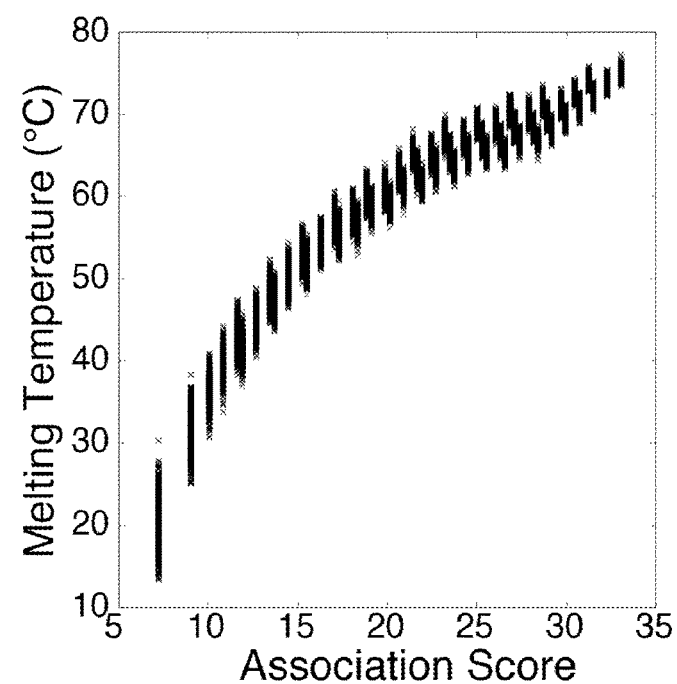
FIG. 9B depicts the melting temperature versus association score ($N=10^5$).
Figure 10:
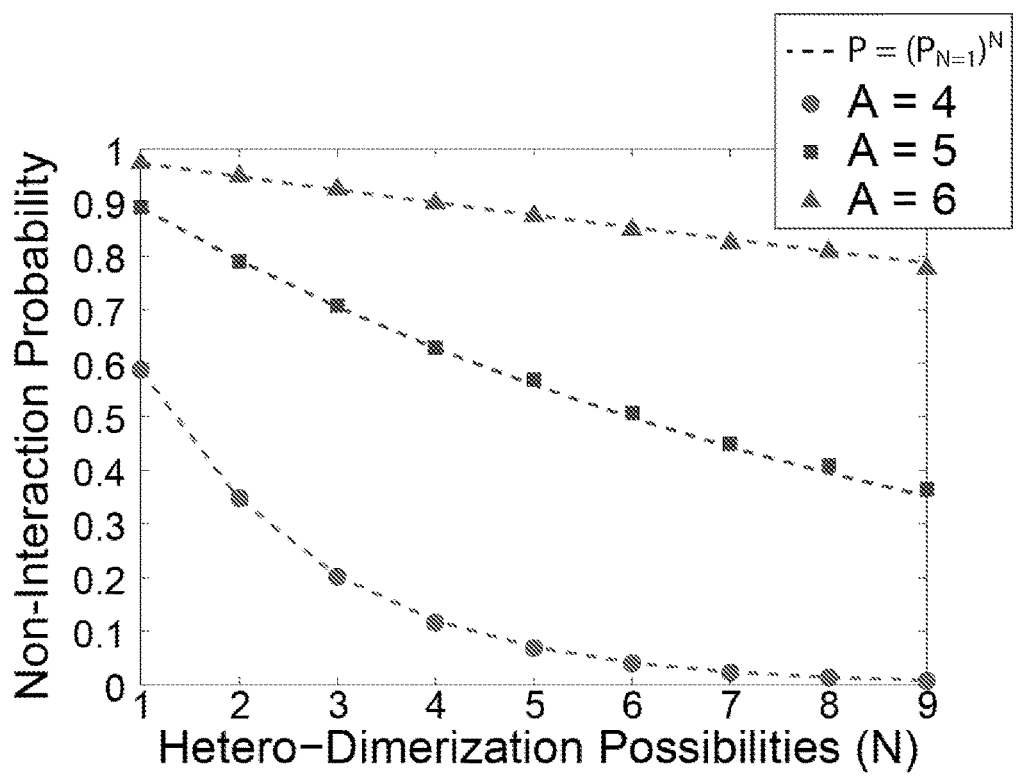
FIG. 10 shows the probability of finding a non-interacting primer versus number of primers in pool parameterized by an association score, which is a measure of the independence of association between primer pool.
Figure 11:
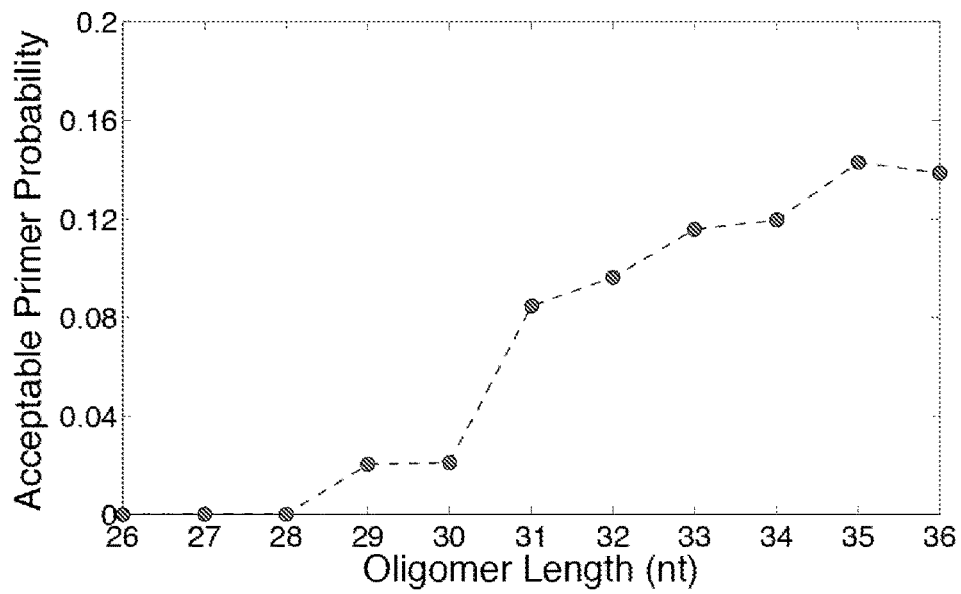
FIG. 11 shows the probability of acceptable oligomers with melting temperature, $T_m$=70±0.5° C. versus oligomer length.

An automated software tool, based on these three steps, to design primers-linkers was developed. Random populations of oligomer sequences were modeled to broadly predict the performance of primer design. The probability of finding a randomized sequence that meets standard primer design constraints occurs between 30-50% of a population of oligomers from 18-30 nt (FIG. 7). Primers meeting this initial criteria range from 20 and 29 nt for $T_m=60\pm0.5°$ C. (FIG. 8). Primer association was scored based on sequence alignment. Higher scores represent higher number of bases associated, with homologous 20 and 30 nt oligomers having scores of $18\pm0.6$ and $27\pm1$, respectively (FIGS. 9A and 9B). It was found that most random oligomers passing basic composition criteria of length 20-30 nt will associate with a threshold score of at least 5 or greater. Primer association in a population was found to be independent and could be predicted as a function of single primer association. These results indicate that a random 20 nt primer should associate with a score of 8 with 95% probability with respect to a pool of 10 primers (FIG. 10). These results are encouraging, particularly since primers can be chosen from a design space larger than the primer size. To assess the effect of design space, the probability of finding two unassociated primers was quantified as a function of dimensionless design space. It was found that as design space increased, the probability of finding an unassociated primer pair increased, predictably. As a result, upstream and downstream design space used to design primers will be between 3 and 4 times primer length. Optimal linker size was determined to be 29 nt based on minimizing linker length while maximizing the rate of acceptable linker sequence generation (FIG. 11). This modeling approach suggest that acceptable primers sets can be found to create information dense constructs. However, kinetic effects are also influential because primers are initially at high concentration with respect to template (~1 μM versus ~1 fM to 1 pM).

To understand and quantify the kinetics of complex PCR reactions, a scalable model was developed to predict PCR products and intermediates and predict linking efficiency. One important but unintuitive conclusion of this model was that the number of amplification cycles to link products appears to asymptote as the number of sites to link is increased. This results because although more sites are linked per construct as sites are increased, there are more options and pathways to form the final product, ensuring it will be possible to create complex constructs from a systematic approach.

Figure 12:
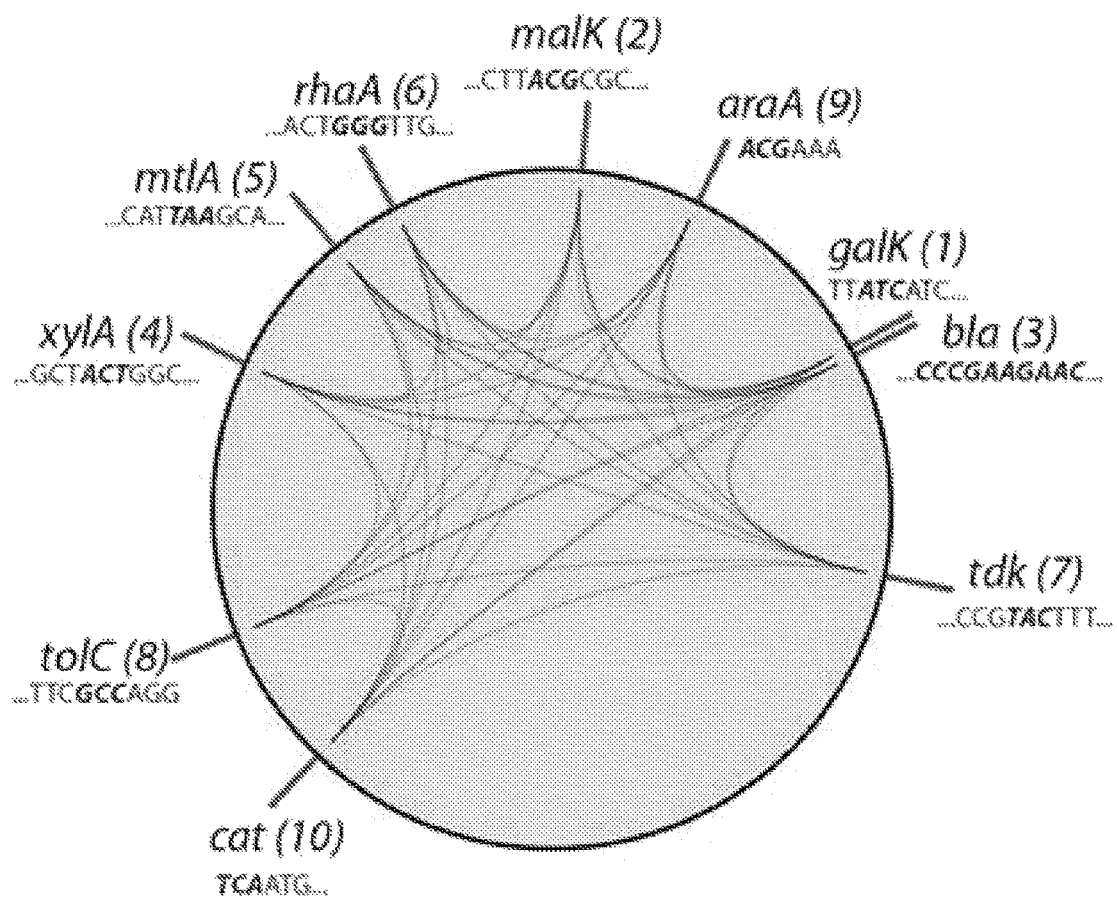
FIG. 12 shows the ten sites in the *E. coli* genome for linking into a large, single construct, with amplified sequences labelled, assessed along with their relative orientation in the *E. coli* genome.

As proof of concept, ten sites were identified across *E. colis* (strain Ecnb2, a derivative of strain Ecnr2) genome (FIG. 12) for stitching and 3 to 6 base pairs were specifically targeted towards condensation. The 10 specific sites chosen appear at the positions indicated in the following table:

| Site Location | Gene | Position |
| --- | --- | --- |
| 1 | galK | 788,768 |
| 2 | kan | 1,255,500 |
| 3 | bla | 808,480 |
| 4 | xylA | 3,728,788 |
| 5 | mtlA | 3,770,304 |
| 6 | rhaA | 4,094,005 |
| 7 | tdk | 1,292,750 |
| 8 | tolC | 3,176,216 |
| 9 | araA | 66,550 |
| 10 | cmR | 2,855,406 |

General Primer Design: Determined good sequences by GC %, no hairpins (as defined by the Matlab function oligoprop and no homopolymer repeats greater than. Temperature was determined by averaging 6 temperature calculations together and primer concentration was $10^{-6}$ M for melt temp.

Statistics: Matlab, alignment. $10^4$ or $10^5$ random sequences that had qualities of good primer design. For percentage statistics, number of primers passing criteria versus no criteria were plotted. Alignment between two sequences was determined by first finding two acceptable primer sequences (GC %, no long homopolymer repeats, thermodynamically unfavorable secondary structure) then determining alignment score.

Kinetic Analysis: Ode15s stiff solver solved the association-dissociationequations with rate constants determined by the basic sequence thermodynamic paramters (enthalpy and entropy). Populations of overlapping and extending segments were updated each PCR cycle.

Primer Design Tool: The design software has 2 parts. A greedy algorithm is used to determine minimum association set by updating number of primers determined by 4 each round. Homology is based on 3' end SDSS method and can be extended to 20. No hairpins, low association with primers and within linkers.

Assembly PCR Conditions: (95-60-72)° C. at (30-45-60) s×35 10× dNTPs; Amplification PCR Conditions: (95-60-72)° C. at (30-30-60) s×14 1× dNTPs.

Emulsion PCR: 5 μL of 10 mM BSA per 100 μL assembly mix, 50 μL mix was added to 150 μL oil (mineral oil, ABIL em90 surfactant and Span 80) followed by a 10 minute emulsification using a miniature stir-bar in a conical bottom 1.5 mL cryogentic tube; water saturated isobutonal extraction then subseuvet size-based gel extraction.

Figure 13:
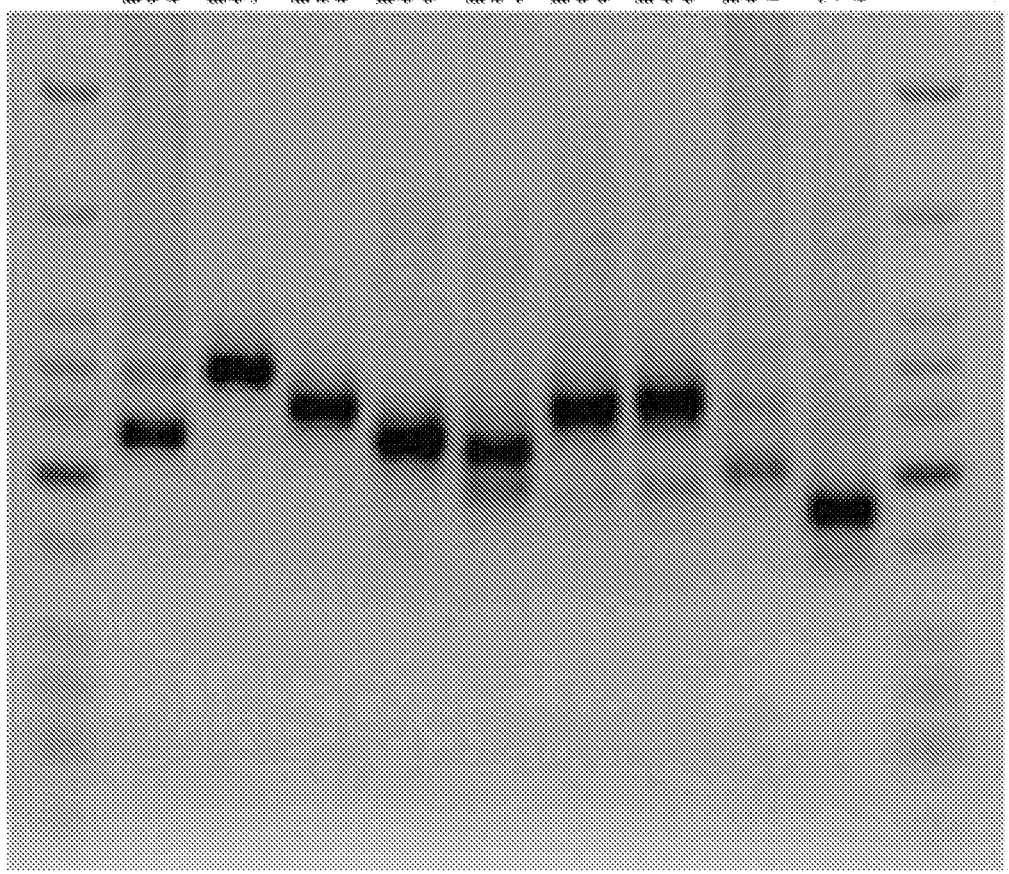
FIG. 13 shows the gel electrophoresis separations assessing the performance of single site amplification for all 10 sites linked in the *E. coli* genome, confirming that all 9 linkers correctly assembled adjacent sites.

Sites chosen were not changed for convenience to further support the broad applicability of this approach. For the 10 sites chosen, the association of designed primer-linkers was no greater than 7, as predicted, and the density of sites in the construct was designed to be 105 bp/site. Single site amplification was tested for all 10 sites and 8 of 10 sites showed efficient and specific amplification, while 2 cases amplified desired product, in addition to being either inefficient or nonspecific (FIG. 13).

Linkers were tested using the linking PCR protocol outlined, and 8 of 9 linking reactions showed specific amplification while 1 site did not show efficient amplification. No relationship between the suboptimal linker performance and single site performance was observed. Using reaction parameters elucidated by kinetic modeling, including a fixed number of assembly cycles (35 cycles) and ten-fold excess dNTPs, large constructs were made to link 3, 6, 8 and 10 sites from 6, 12, 16 and 20 primers, respectively. After amplification, bands were observed for 3, 6, 8 and 10 sites at expected sizes. Sanger sequencing returned the expected results. Sequencing errors were randomly spread throughout the roughly 1 kb, 10-site construct at 1% (10 errors), with two errors occurring in the amplified template region and 8 errors occurring in the primer-linker region. Re-sequencing corrected for these errors, suggesting that perhaps better sequencing primer design or DNA purification will yield consistent results.

Linking distal genomic sites, ultimately will be useful for tracking combinations of mutations that occur in populations of cells. Three sites were linked (galK, kan, bla) in two strains (ecnb2 and ecnb15) which were generated through a MAGE process to introduce mutations in galK and bla. Using this stitching process and Sanger sequencing, the genotypes of mutants were identified. Mixing these populations and sequencing lost all combinatorial mutation information. By performing the stitching reaction in an oil emulsion and sequencing products using high-throughput sequencing, the combinations of mutations found in a population, as well as the relevant frequency of these combinations were determined.

This example demonstrates that the systematic approach to primer and linker design in conjunction with an understanding of the multiplexed linking PCR chemistry, can be successfully used to rapidly and inexpensively genotype combinations of mutations that occur in single genotypes or diverse populations.

Opportunities exist to further define the automated approach of primer design and to improve linking performance from a reliability and efficiency standpoint. This technology can be used to rapidly screen MAGE populations and elucidate details of epistasis in MAGE libraries, which can drastically improve a priori engineering efforts. From a population level approach, limitations in high-throughput sequencing read-lengths influence the quantity of sites that can be studied, although methods exist to overcome read-length limitations and certainly future technological advancements will expand sequencing read-lengths. Furthermore, this technology is not limited to bacterial systems, and may find utility to rapidly genotype eukaryotic cell lines where multiple mutations have been shown to create deleterious conditions such as cancer.

Example 3

Linking genomic sites, as exemplified in Example 2, relies on the ability to extend orthogonal homologous segments in parallel using a multiplexed primer pool, while mitigating undesirable interactions. This problem is inherently complex, involving intermediate species, non-linearly changing species concentrations as the reaction proceeds and undesirable interactions occurring by nature of the complexity of the species pool. Beyond understanding the thermodynamics, which contribute part of the complexity of multiplexed linking PCR, understanding the reaction conditions and dynamics that arise when amplifying from diverse primer pools is critical towards understanding and engineering protocol towards reliably creating desired constructs.

The kinetics of PCR processes are typically modelled to predict the efficiency of quantitative DNA amplification technologies like quantitative PCR. For amplifying a single site, these models use 7 ordinary differential equations (ODEs) describing the association-dissociation kinetics of species present in the reaction. Along with consideration of nucleotide consumption and polymerase activity, this reaction engineering approach has been shown to accurately quantify qPCR efficiency. In addition to modelling single PCR reactions, the association-dissociation kinetics of complex primer pools have been studied using microarrays. With a diverse DNA pool hybridizing, these pools act as multiplexed systems and the complexity of the process can be captured with a three-equation kinetic system describing primary hybridization, competition and background. Although accurate models exist towards understanding amplification of single targets and understanding the hybridization kinetics of known systems, the analysis of complex PCR conditions which arise during multiplexed linking PCR have not been addressed. The inherent non-linearity of such a system is challenging to model because the number of species increases in a quartic relationship with the number of sites linked. This limits direct assessment of the kinetics and therefore a general approach must be developed to describe this increasing complexity.

A generalized kinetic modeling approach is developed to understand the complexity that arises from multiplexed linking PCR and understand how to appropriately tune reaction condition to attain optimal linking performance. Linking of up to 6 different sites are modeled over 40 cycles, involving a maximum of $2 \times 10^4$ ODEs to be simultaneously solved for. This approach allows for the dynamics of species concentrations to be tracked and analyzed versus changing reaction variables. These results are used to determine optimal reaction conditions and to generalize the complex phenomena occurring in multiplex linking PCR. Furthermore, specificity of dNTP utilization is used to assess the efficiency of end product being consumed. Finally, the conclusions from this model are experimentally supported with qualitative results.

In a model multiplexed linking PCR process for 2 sites, generally, 2n primers, containing n−1 unique linkers are used to link n sites and create a construct. A numbering scheme was used to mechanistically determine overlap, association and general model calculations. Each independent piece is given a number corresponding to its position on the final linked strand from 5'-3' in the sense direction. For example, when linking 2 sites, a final construct contains 1 linker connecting the two sites. Numbers 1 and 3 correspond to sites 1 and 2, respectively. Number 2 corresponds to linkers between sites 1 and 2.

For simplicity, the model assumes that initial template is free and can be consumed to create higher order products. Based on the number of primers, template and linker, the minimum number of species, N, present during a reaction is determined by Equation 1:

$$N_{species} = 4n_{sites}^2 - 2n_{sites} + 2 \qquad (1)$$

The number scheme used to number constructs is used to index all possible species and used to predict the existence of these species and calculate extension between species.

To determine the species concentrations changing with time, a three-step model of dissociation, annealing and extension was used to represent a single PCR cycle. The first step of dissociation is at high temperature (T=94° C.) sets initial conditions where the system has no hybridization events, and only single-stranded species exist. Annealing is then determined by solving a system of ODEs based on Equations 2-4 from an initial time (t=0) to an anneal time (t=$t_a$). Equations 2-4 correspond to the hybridized species balance, the sense species balance, and the antisense species balance, respectively. The differential terms are the change of species with respect to anneal time which is balanced by the generation and loss of species through hybridization.

$$\frac{\partial \bar{\bar{C}}_H}{\partial t} = k_a \bar{\bar{\lambda}} \circ \left( (\underline{C}_a^T \underline{C}_s) - \bar{\bar{K}}_D \circ \bar{\bar{C}}_H \right) \qquad (2)$$

$$\frac{\partial \underline{C}_s}{\partial t} = \underline{1} \left( \bar{\bar{\delta}} \circ \left( \bar{\bar{C}}_H^T (k_a \bar{\bar{\lambda}} \circ \bar{\bar{K}}_D) - (\underline{C}_s^T \underline{C}_a)(k_a \bar{\bar{\lambda}}) \right) \right) \qquad (3)$$

$$\frac{\partial \underline{C}_a}{\partial t} = \underline{1} \left( \bar{\bar{\delta}} \circ \left( (k_a \bar{\bar{\lambda}} \circ \bar{\bar{K}}_D) \bar{\bar{C}}_H^T - (k_a \bar{\bar{\lambda}})(\underline{C}_s^T \underline{C}_a) \right) \right) \qquad (4)$$

Description of parameters and matrix sizes is provided in the following table:

| Variable | Size | Description |
| --- | --- | --- |
| J | 1 × N | Compatible vector of ones |
| δ | N × N | Identity matrix |
| $C_s$ | 1 × N | Sense strand species concentration vector |
| $C_a$ | 1 × N | Antisense strand species concentration vector |
| $C_H$ | N × N | Hybridized species concentration matrix |
| λ | N × N | Boolean association matrix |
| $K_D$ | N × N | Equilibrium matrix with values defined as $k_d/k_a$. |

For simplicity, it is assumed that hybridization only occurs between corresponding sense and antisense segments. For example, primer 1 forward only anneals to the primer 1 reverse site. These forward and reverse sites can be located on many species. In addition, other hybridization events, like formation of hairpins and dimers are ignored in this model. The third step of the model is the extension of hybridized species by the DNA polymerase and is assumed to be 100% efficient throughout the duration of the reaction. Current estimates assume a 1% decrease in activity per cycle, which would not compromise the modelled reaction progression.

Annealing concentration models were solved in MATLAB using ode15s, a stiff ODE solver to determine the concentration of species and intermediates based on equations 2-4. Solver parameters included a maximum time step of 10 ms, and error tolerances of $\epsilon_{abs}=2\times10^{-4}$ and $\kappa_{rel}=6\times10^{-8}$. At the end of the set anneal time (30 s unless otherwise noted), hybrid concentrations are extended. Hybrid extension has four possibilities. These possibilities include a sense only extension, anti-sense only extension, sense and anti-sense extension or no extension. The degree and length of extension was determined based on the numbering scheme. Naturally, the total number of species must be conserved between PCR cycles and this was one metric used as a basis for determining the model performance.

Boolean association matrices and kinetic parameter matrices were determined based on the number of sites and association. An example association matrix is depicted in FIG. 1c where black squares represent association and a value of 1, and white squares are no association and a value of 0. The columns are based on the sense direction and rows are based on the anti-sense direction. Association is determined based on overlap of the numbering for rows and columns. Primers are located at the right of the matrix (for the forward primer) and bottom of the matrix (for reverse primers). $C_s$ and $C_a$ correspond to the sense and antisense vector [1×N] and their product ($C_a^T C_s$) corresponds to elements in the association matrix. By performing an element-by-element multiplication of the association matrix, what remains is a product of the expected associated species in this system.

Kinetic parameters were determined based on a calculated thermodynamic equilibrium of species present using MATLAB's oligoprop function contained in the bioinformatics toolbox. Thermodynamic parameters (ΔH, ΔS) were used to determine ΔG through Equation 5.

$$-R_g T \ln(K_D) = \Delta G = \Delta H - T\Delta S \quad (5)$$

Four free energies were calculated using different sets of nearest-neighbor thermodynamic parameters. The mean of the four calculated free energies were used to determine the equilibrium parameter between two species. This equilibrium value was equal to the ratio of the rate of association versus dissociation. It was assumed that association rate was equal for all species ($k_a=10^{-6}$ s$^{-1}$). To generalize the model, generic primer, linker and template were used for all priming, linking and template sites. Since the model did not consider undesired interactions and hairpins, this approach was compatible. Final constructs were simply concatemer of forward-template-reverse-linker.

PCR was performed using 1% v/v Phusion™ Taq Polymerase, 1.5 mM MgCl$_2$ salt, 20% v/v 5× Phusion™ buffer, 100 µM concentration of dNTPs and primers (typically total 2 µM concentration). Template was extracted from ecnb2 culture grown overnight from a freezer stock in chloramphenicol (3.4 µg/mL) using a PureLink™ Genomic DNA MiniKit. DNA was quantified using a Nanodrop and the total DNA concentration was diluted to an appropriate concentration (typically 1 pM). For linking 3 sites, 6 primers are used, and each is at 330 nM concentration.

Assembly was performed using a three-step denature-anneal-extend thermocycling protocol for a desired number of cycles. When assessing the cycle effect on assembly, a 50° C. hold step was used between extension and denaturing steps to remove desired samples in the case of variable assembly cycles. Following assembly, amplification PCR was performed for a low number of cycles (10-12) using 5% assembly PCR product and outer construct primers to ensure linear DNA amplification for more accurate assessment of product concentrations. Experiments were performed in triplicate and mixed prior to final separation and analysis. For experiments comparing a changing parameter one stock solution was used to ensure uniform starting conditions. Separation was performed using 1×TAE agarose gel (1.5%), with a 100V potential for 30 minutes.

Two stages of amplification are observed: 1) an exponential amplification regime and 2) an asymptotic final regime resulting from decreased primer concentration and increased final product association. As would be expected, the model predicts that as more sites are linked, final product requires more cycles to form. This lag is based on forming necessary precursors of the final construct in high enough quantities to have appreciable interaction kinetics. Another feature that is apparent is that the transition from exponential amplification to asymptotic appears more gradual as the number of sites is increased. Finally, the increase in cycles to attain a threshold concentration between sites becomes shorter as the number of sites increases.

Qualitatively comparing experimental results to model results for three sites appears to be in good agreement for predicting the exponential phase. However, a decrease in construct concentration is observed as cycles increase into the asymptotic phase. This occurs because the model predicts the final construct as the last product that can be made. Realistically, other unpredicted and undesirable interactions can occur which consume the final construct, and necessitate requiring an optimal number of cycles.

Figure 14:
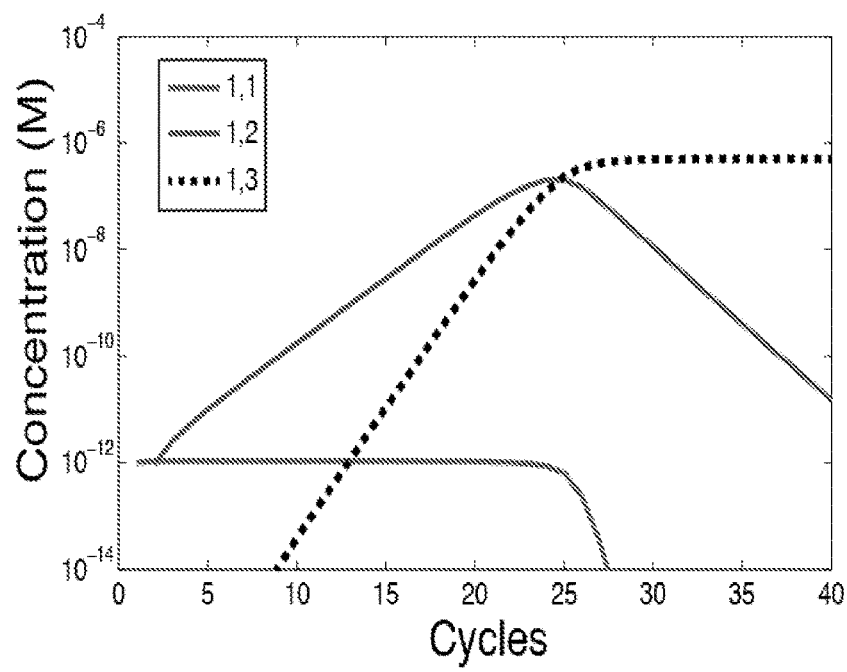
FIG. 14 shows the plot of final products and intermediates to 2 linked sites in order to assess the prediction of more gradual transitions to an asymptotic phase.
Figure 15:
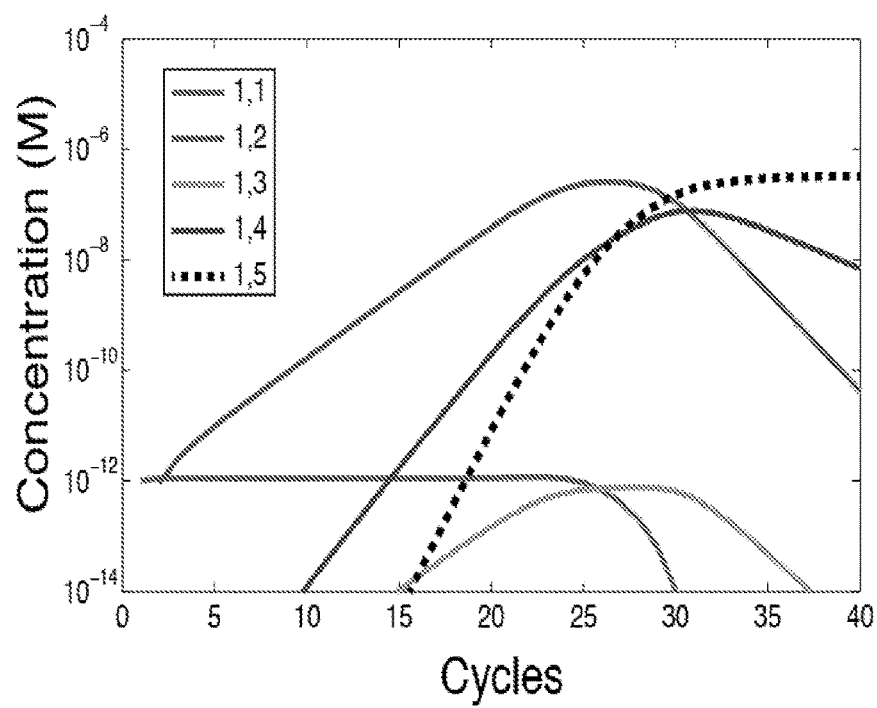
FIG. 15 shows the plot of final products and intermediates to 3 linked sites in order to assess the prediction of more gradual transitions to an asymptotic phase.

Assessing the species landscape provides valuable insights into the dynamics of linking PCR and can also be used to explain many of the observed properties that arise as more sites are linked. To assess the prediction of more gradual transitions to an asymptotic phase as more sites are linked, final products and intermediates are assessed, and plotted in FIGS. 14 and 15 for 2 and 3 linked sites, respectively. Two sites has the most abrupt transition from exponential to asymptotic generation of final product relative to larger sites. This is observed to correlate as the intermediate is net-consumed. The inflection point of product generation, directly corresponds to the maximum of intermediates. The three site case demonstrates the dynamics of a more gradual transition. In this case, several pathways can be taken towards generating final product. The net-consumption of corresponds to the transition towards asymptotic production. However, species is still net generated, which delays asymptotic production. In both cases, template is consumed as final product concentration is large enough since it is assumed to be free template.

The fact that more intermediate species contribute towards forming higher order products as the number of sites to link increases, can explain the observed phenomena of the number of cycles reaching a final construct size appears to asymptote as the number of species is increased. Although the complexity of forming larger constructs is greater for more sites, the number of pathways to form these products also increases to alleviate limitations arising from a linear pathway.

Figure 16:
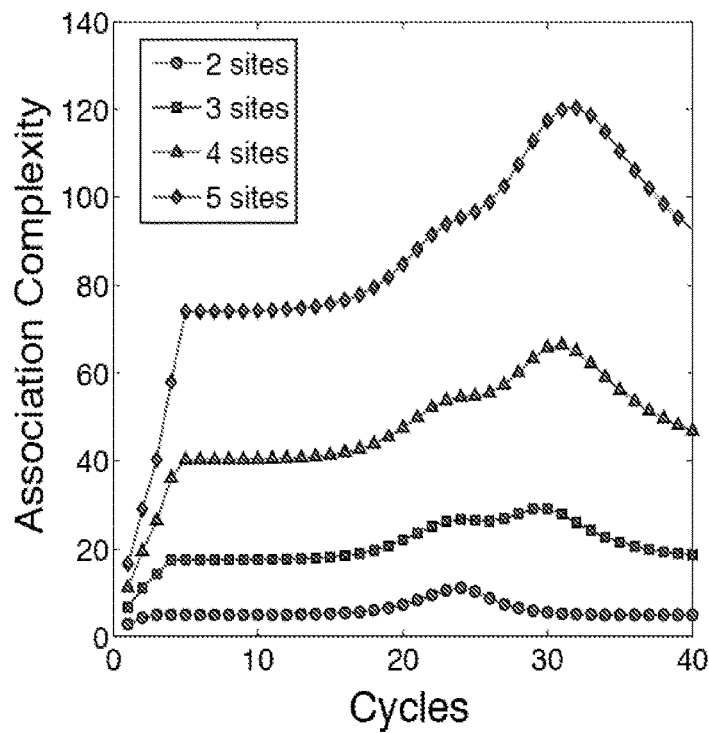
FIG. 16 shows complexity versus cycles plotted for several linking reactions.

To describe the diversity of interacting species, a complexity term defined in Eq. 6, is used where N is the number of interacting species and $p_i$ is the probability of selecting species i from the pool. This equation is also equivalent to the Gibbs entropy, although here, values only roughly account for interacting species (polynucleotides) with no confirmational of volume considerations. As a greater number of interacting species are present in equal numbers, the system increases in complexity. A complexity landscape is formed as products are generated and consumed each cycle. A few notable features are present (FIG. 16). As expected, complexity is greater when amplifying more sites. The peak at two sites corresponds to high concentration of final product and intermediate, while the decrease at 35+ cycles corresponds to the net consumption of intermediate. In higher order cases (3+ sites), a shoulder-peak feature is observed. The shoulder occurs as primer and template are amplified enough to have an appreciable impact on the species concentration profile. The second peak represents higher-order products being formed. Interestingly, the second peak seems to shift towards higher cycles as more sites are linked. Finally, as all species converge towards a final product, the system's complexity further decreases. Realistically, this may not be the case as larger amounts of product would interact in unanticipated ways, diverging towards a diverse and unpredictable species population.

$$C = -N\sum_i p_i \ln(p_i) \tag{6}$$

Figure 17:
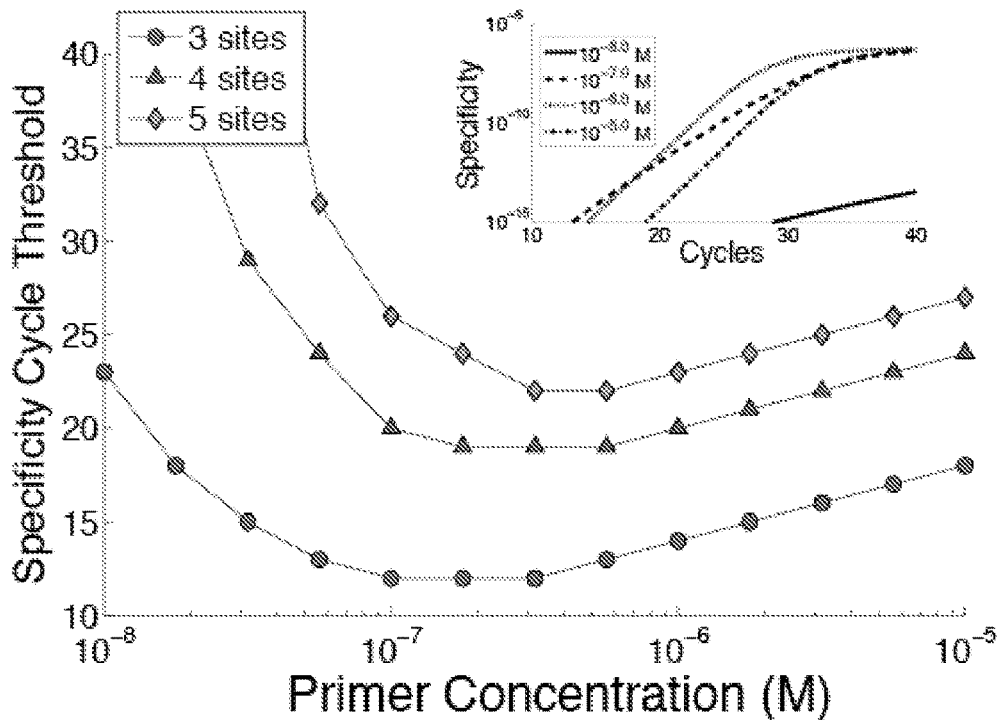
FIG. 17 shows a plot of specificity threshold of a reaction versus different primer concentrations.
Figure 18:
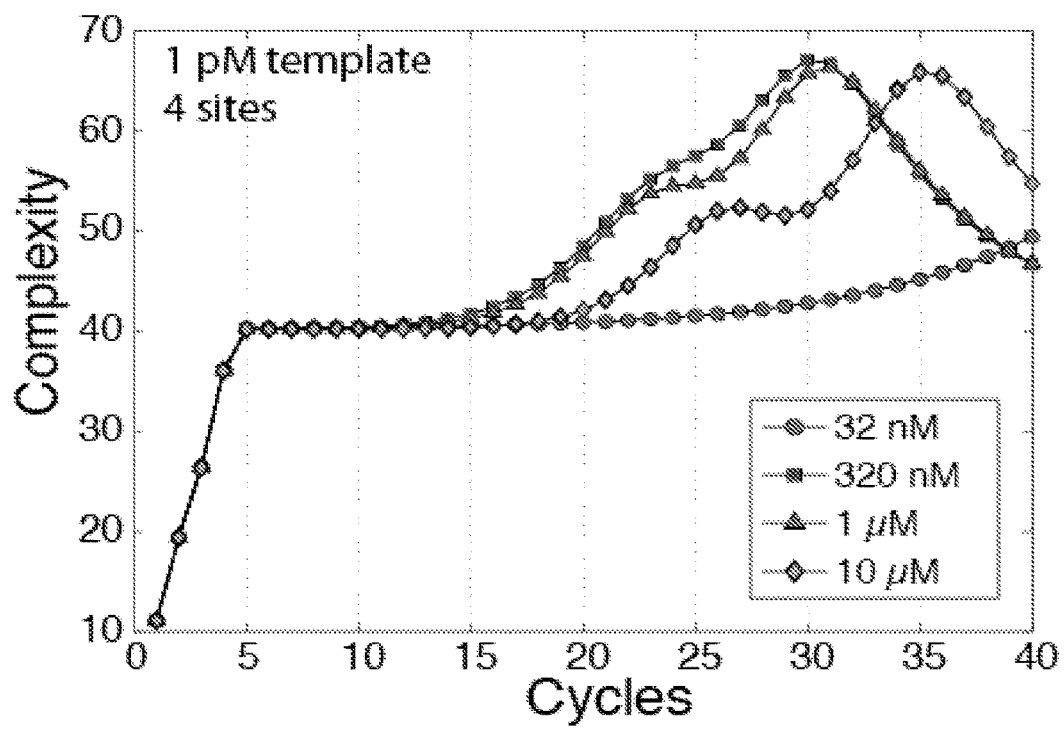
FIG. 18 shows a plot of complexity versus cycles at various primer concentrations.
Figure 19:
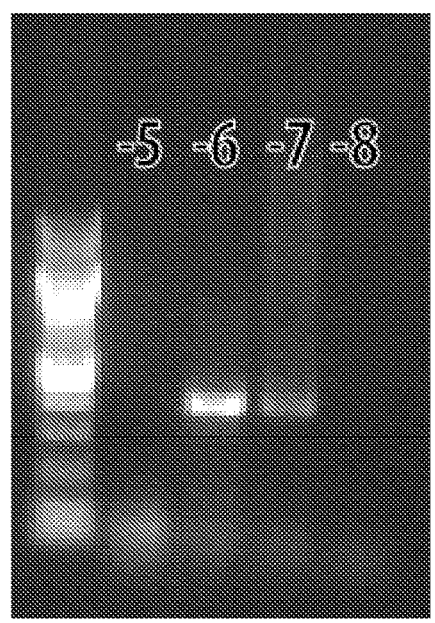
FIG. 19 shows an agarose gel image of three site construct amplified after a variable amount of total primer concentration. The primer concentration exponent (10^x) is labelled above each separation lane.

By the nature of highly multiplexed PCR reactions, undesirable interactions are unavoidable between primers. Depending on the magnitude of undesirable interactions, this can severely compromise the generation of end products oftentimes presenting a barrier to product generation. Potentially, nucleotides can be consumed prior to even forming product. Therefore, the quantity of final construct versus nucleotides consumed (referred to as specificity) was quantified for a variety of conditions. Realistically, a higher specificity at lower cycles would favor the most efficient generation of final construct. The first metric used to assess specificity, was a threshold, which is the fewest number of cycles required to achieve a specificity of $10^{-14}$. When plotting specificity, threshold versus primer concentration an optimal value exists, where too high or too low of primer concentrations are less efficient at producing final product (FIG. 17). When viewing the reaction complexity versus cycles, this trend is also observed where the complexity rises more quickly at the optimal primer concentration, and displays a less pronounced shoulder when compared to higher primer concentrations (FIG. 18). Experimentally, this could be observed, that 10 µM and 10 nM primer concentrations do not form final constructs nearly as well as the 100 nM to 1 µM range (FIG. 19). It is also observed that at the 100 nM range, there seems to be nonspecific product after amplification (represented by a larger streak following the band). Finally, at the 10 µM primer concentration, a large amount of dsDNA exists around the 100 bp range, which results from the large amount of intermediate products transferred between reactions.

The optimal specificity can be understood by examining the progression of intermediate species at variable primer concentrations. At low primer concentrations (32 nM), product does not form rapidly enough to form intermediate products. The resulting primer-template association kinetics are low and the chance of intermediates associating is unlikely with respect to reactions containing higher primer concentrations. With optimal primer concentrations (320 nM), final products and intermediates are observed to grow and initial primers substantially decline as the reaction proceeds. At high concentrations of primers (10 µM), the final and intermediate product also appears to grow, however, the initial primers and smaller intermediate species remain at high concentration, subsequently diverting nucleotide flux from assembling intermediate species to generating intermediate species.

Figure 20:
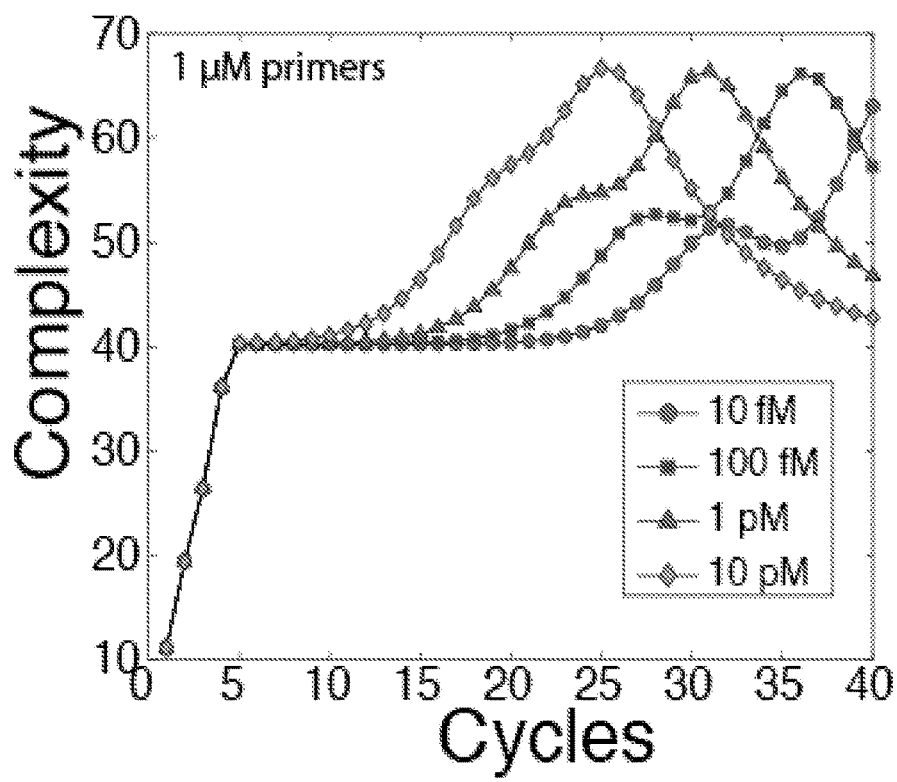
FIG. 20 shows a plot of complexity versus cycles with varying template concentrations.
Figure 21:
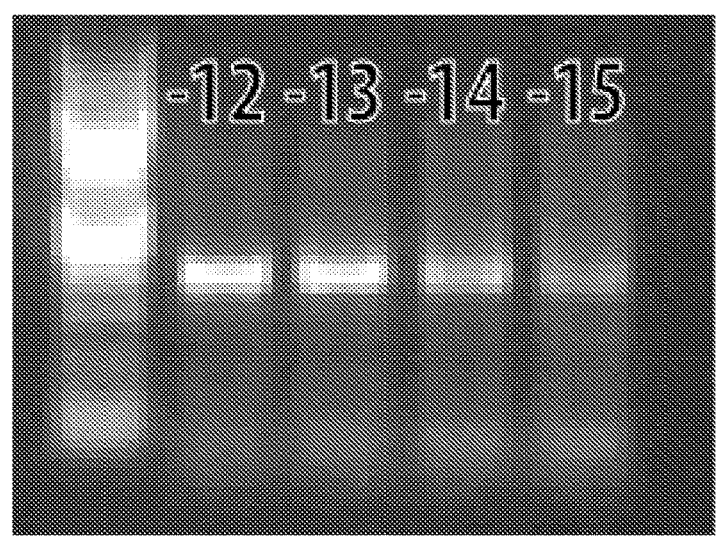
FIG. 21 shows an agarose gel image of three site construct amplified after assembly with variable amount of template concentrations. The template concentration exponent (10^x) is labelled above each separation lane.

Template concentration is a reaction variable that arises particularly in cases where the linking reaction is performed on single cells, and also greatly affects the extent of construct generation that can be performed. It is found that the lag time before the peak in the complexity curve shortens with increasing primer concentration (FIG. 20). This is expected because intermediates can accumulate more quickly from a higher concentration starting point. In addition, as template is reduced, the curve appears to have a larger shoulder which eventually transitions into a second peak. This transition was also seen in suboptimal primer concentrations (FIG. 18) and suggests that not only do higher initial template initiate more efficient stitching reactions, but they also direct nucleotides towards final product more efficiently. Experimentally this could be observed (FIG. 21) where higher template concentrations (100 fM to 1 pM) are far brighter with respect to each other and to background concentration than lower template concentrations (1 fM).

Figure 22:
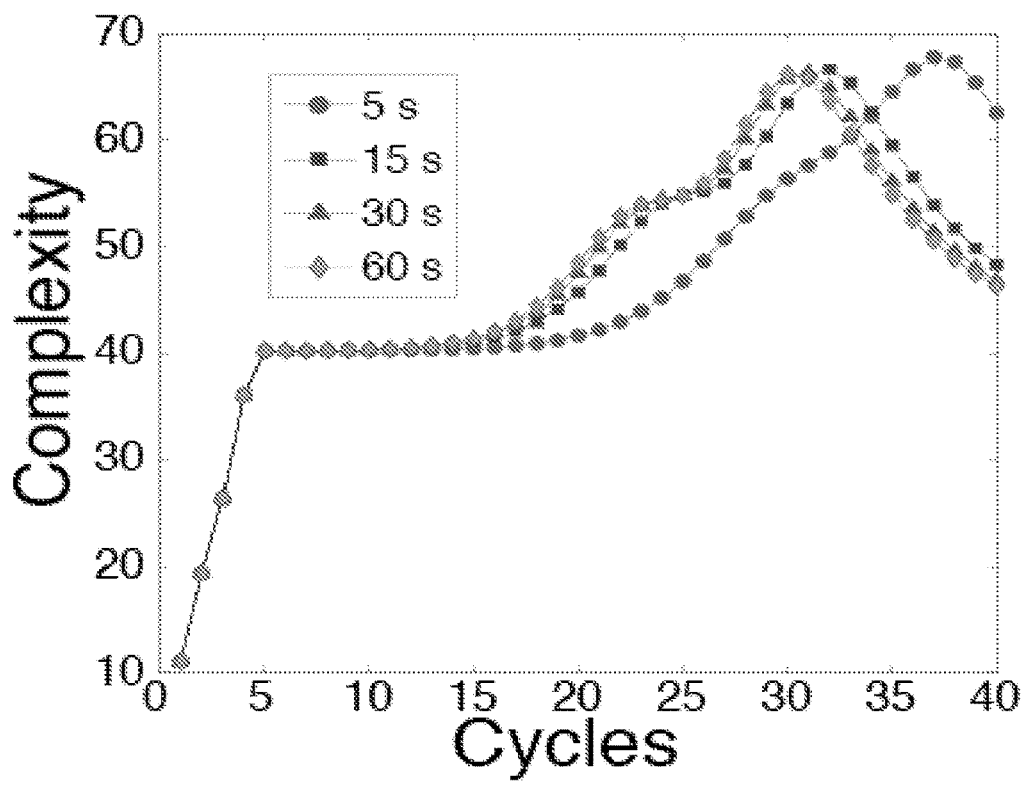
FIG. 22 is a plot of complexity versus cycles with varying annealing times.
Figure 23:
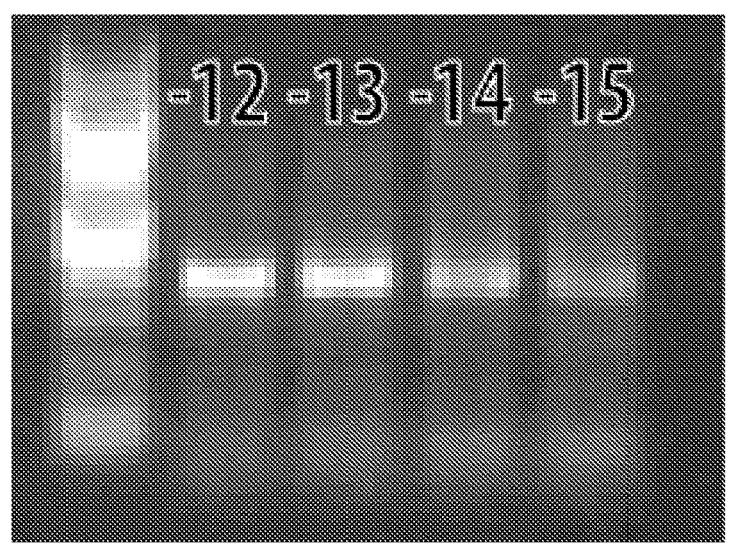
FIG. 23 shows an agarose gel image of three site construct amplified after assembly with variable annealing times.

Anneal time can also control the efficiency of the linking reaction by controlling the relative rates of association and dissociation between species during the annealing phase. From a complexity standpoint, it appears that short anneal times (5 seconds) severely compromise performance (FIG. 22). Whereas above an intermediate anneal time (15 s), it is predicted that performance should be near equal, slightly favoring longer annealing times. Experimentally it was found that increasing annealing time increases linking performance (FIG. 23). However, the degree that annealing time affects performance seems to be underestimated. This is likely due to annealing time affecting nonspecific interactions that were not included in the model.

This example demonstrates that assessing the kinetics in these complex reaction conditions by designing a general approach towards modelling, reactions are understood on a deeper level. The inventors found that by controlling reaction parameters like cycles, species concentrations and hold times, linking PCR performance could be controlled and improved. Consequently, it was found that optimal cycles, and primer concentrations exist. It was also found that complexity could be used to assess the species landscape. Opportunities exist to further improve the modelling effort by including ways to predict non-specific amplification, or even include a general non-specific amplification term. Other questions of temperature profile, primer concentration profiles and primer design can be assessed. Results of this model can be used in conjunction with thermodynamic primer design tools to reevaluate and tune primer design. Finally, general models like this can be used towards assessing other multiplex DNA amplification technologies like gene synthesis and MASC PCR.

Example 4

To demonstrate the broader applicability of TRAcking Combinatorial Engineered libraries (TRACE), the inventors assembled and amplified independent 4-, 8- and 9-site constructs from an *E. coli* combinatorial mutation library as well as heterozygous BRAF and MEK mutations in human ES2 ovarian carcinoma cell line. The inventors also optimized reaction conditions (via DMSO/Betaine gradient search) to find a reaction condition that works for a broader range of systems. The optimized reaction conditions resulted in successful assembly of three of the four independent sets. Moreover, the 8-site construct was assembled under both optimized (displaying a faint band on agarose gel electrophoresis) and unoptimized reaction conditions. The inventors expect that the 8-site set was more challenging to assemble than other sets because of possible primer-primer interactions, which can be reduced with more stringent primer design conditions and/or optimization of reaction conditions. It is important to note that although the desired product bands appear may heterogeneous under the single set of assembly conditions employed, there are several options available to ensure accuracy and maintain throughput, including optimizing the assembly conditions for a specific construct, sequencing as is, addressing computationally, and/or performing gel extraction using high-throughput commercial technologies.

Example 5

Figure 24:
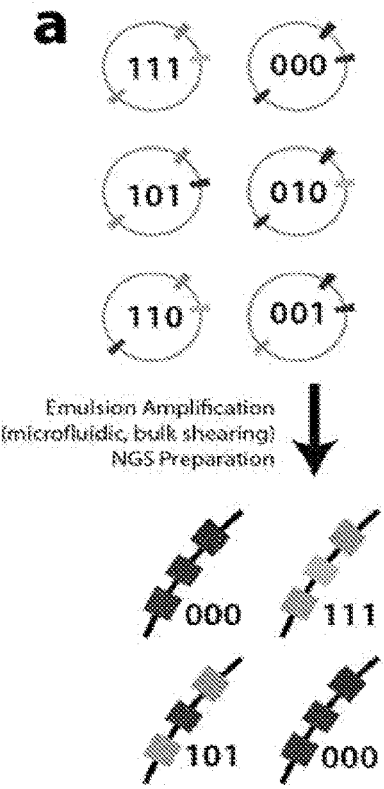
FIG. 24 shows a schematic of the approach for tracking an artificial combinatorial population using next-generation sequencing. Six genotypes are generated via recombineering modified at three sites (galK-kan-bla) to be either on (1) or off (0). Assembly is performed in emulsions to generate a construct set representing the original population.
Figure 25:
FIG. 25 is a graphical representation of observed genotypes versus varying η for an initial population of two unequal genotypes. In this case the middle genotype is not considered in the calculation since it does not vary.
Figure 26:
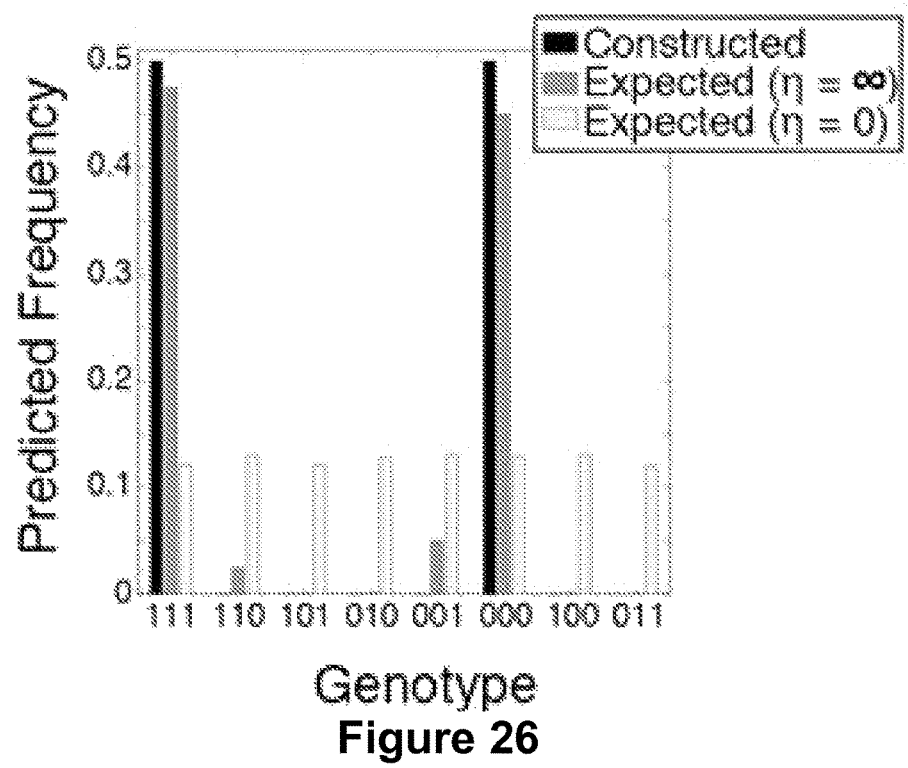
FIG. 26 is the constructed population frequency of genotypes created assuming pure strains and constant cell count to $OD_{600}$ between strains. Expected (η=∞) refers to expected population no crossover occurs. Expected (η=0) is the expected result assuming the observed signal is all crossover.
Figure 27:
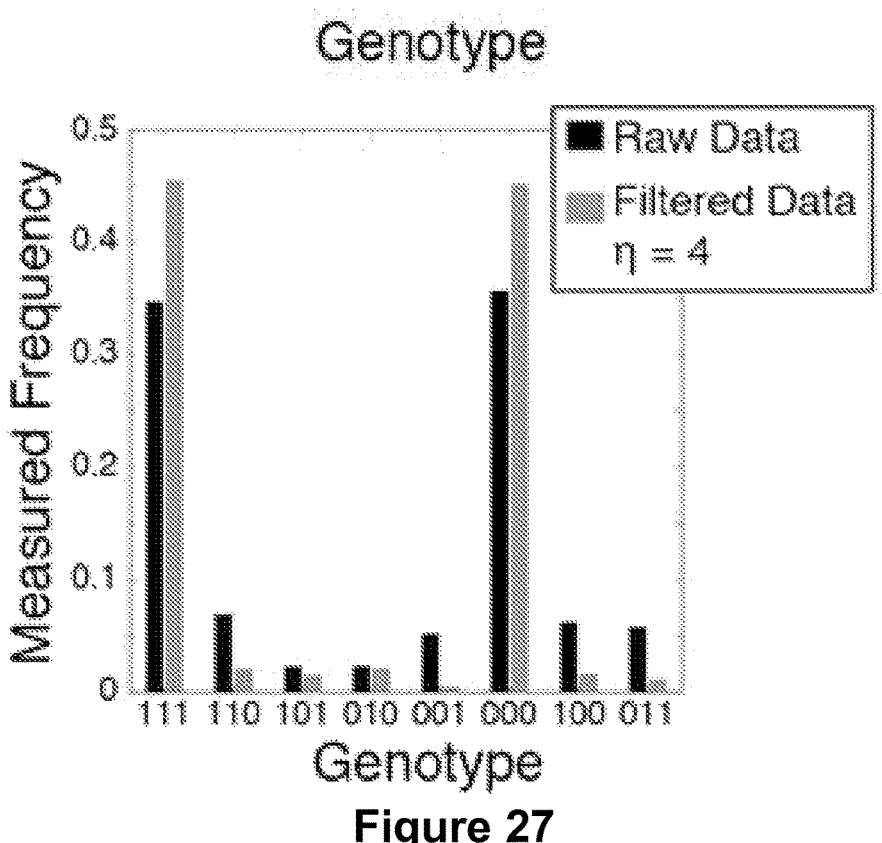
FIG. 27 shows the experimental TRACE results on the constructed population. Filtered data assumes η=4.

Although TRACE performed on single colonies, advances the capabilities for efficiently genotyping of distal genomic loci, the primary impact of the processes of this disclosure is the ability to perform tracking on a population scale using high-throughput sequencing (e.g. Illumina MiSeq™). To demonstrate population-wide tracking, the inventors adapted TRACE to an emulsion-PCR format where individual cells are isolated in picoliter droplets that enable parallel assembly across an entire population at single-cell resolution (~$10^9$ reactions/mL). Droplet assembled sequences are then prepared for high-throughput sequencing by size selection and a minimal level of additional PCR amplification to append the 5' and 3' ends with Illumina sequencing adapters. Assembly was verified to work in an emulsion format by assembling the 10-site construct described in FIG. 12 and size verifying the extracted and amplified construct through gel electrophoresis. To demonstrate the effectiveness of this approach, synthetic mutant populations were constructed by recombineering specific on (1) or off (0) mutations at three sites (galK-kan-bla) (FIG. 24); for a total of six constructed genotypes. In the first test, strain 111 (EcNB2) and 000 (EcNB15) were mixed in equal proportions as measured by optical density and then TRACE in emulsion format was used to count the number of 111 and 000 genotypes in the mixed population. High-throughput sequencing demonstrated that most sequences (over 90%) were correctly assembled. The key issue here is the ability of TRACE to specifically assemble individual genotypes within the isolated environment provided by the emulsion (i.e. Signal) relative to the non-specific assembly of multiple genotypes due to various potential factors such as droplet merging, multiple cells per droplet, or template crossover in post-emulsion PCR steps (i.e. Noise). The inventors defined a TRACE signal to crossover noise ratio (SNR or η) as the ratio of actual genotype counts to the expected genotype counts assuming all sites are independently interacting (FIG. 25). In the absence of emulsification, $\eta=0$ and a near-uniform distribution of all eight possible genotypes is predicted (FIG. 26), while at $\eta=\infty$ there is no-crossover and the initially mixed populations frequencies are accurately reproduced. As expected, the emulsification strategy employed here reduces crossover sufficiently to recreate the expected population distribution (FIG. 27). Any low-level of sequence crossover likely occurred during the bulk PCR steps required when preparing constructs for sequencing, which the inventors minimized through in vitro DNA repair and longer PCR extension times, and could be further reduced by performing such steps in emulsion. Without in vitro repair and long extension times, the TRACE SNR was close to 0 and population heterogeneity was indiscernible. Differences between measured and expected genotype frequencies can be explained assuming crossover noise is present and the inventors could correct for the noise assuming a crossover SNR of $\eta=4$ (qualitatively the signal outweighs the noise by a factor of four; FIG. 27).

Figure 28:
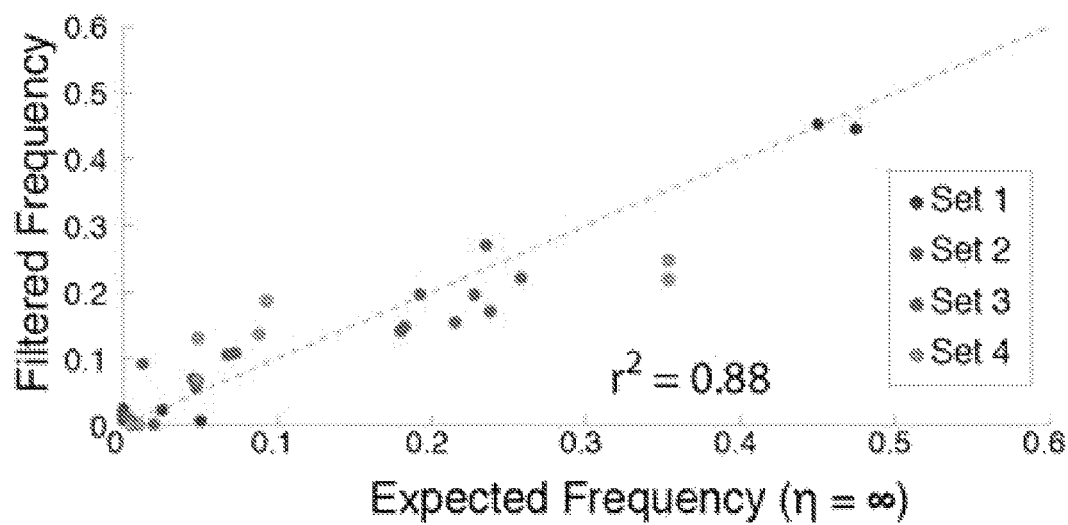
FIG. 28 shows the measured genotype frequency versus corrected population for four populations assessed from the combinatorial assembly.
Figure 29:
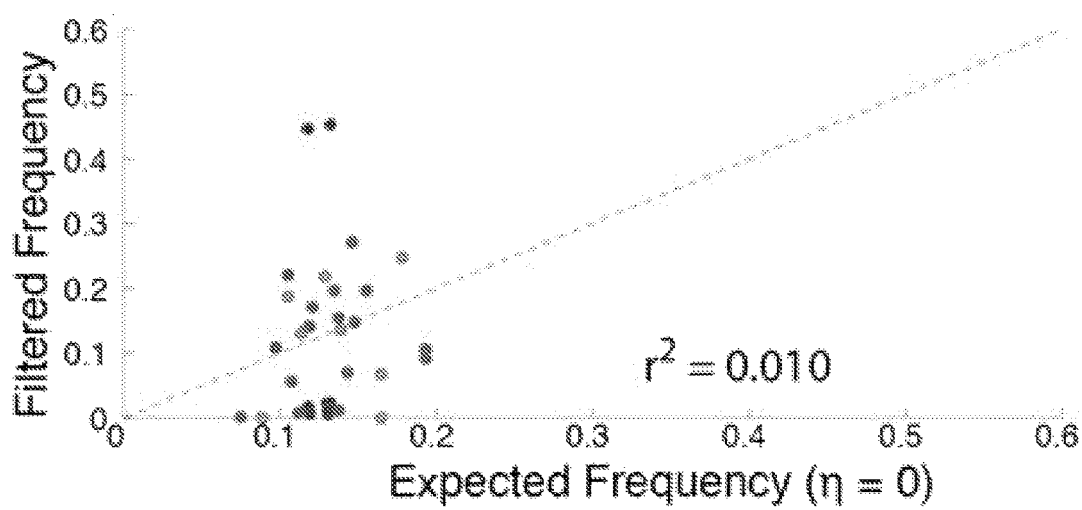
FIG. 29 shows the same population data from FIG. 28 to display measured genotype frequency versus the full crossover prediction.

The inventors performed additional synthetic population tracking studies with up to six different combinations of specific genotypes evaluated. A significant linear correlation was observed between expected population frequency (based on optical density) and the population frequency obtained by TRACE assuming a $\eta=4$ ($r^2=0.88$, $p<10^{-3}$) (FIG. 28). Moreover, no trend is observed when comparing the expected population frequency assuming full crossover ($\eta=0$) to the measured output population frequency (FIG. 29, $r^2=0.01$). These results clearly demonstrate TRACE is quantitative and compatible with high-throughput sequencing technologies that enable population-scale tracking. Quantitative deviation between the measured and expected results are likely due to difficulty of creating exact synthetic populations, where the variability of $OD_{600}$ to cell count is known to fluctuate by several fold. Moreover, individual genotyping experiments using high-throughput sequencing showed low levels (5-15%) of background mutations which may be present in the population due to incomplete chromosomal segregation after recombineering.

Example 6

The studies demonstrated in Examples 1-5 were performed on synthetic populations constructed to aid in the development and optimization of TRACE. In the studies of this Example, the inventors applied TRACE to the tracking of more realistic systems comprised of combinatorial libraries generated by recursive multiplex recombineering (e.g. MAGE). The inventors first evaluated a combinatorial library constructed in *E. coli* strain SIMD70 where ssDNA was designed to modify the RBS of 27 different targets. In prior evaluations of this library, the inventors were unable to identify combinatorial mutants using conventional approaches (MASC-PCR, individual colony/RBS sequencing) and due to the low throughput of such approaches could not conclude if such combinatorial mutants did not exist at all in the library or were simply at a frequency lower than predicted based on reported recombineering frequencies.

Figure 30:
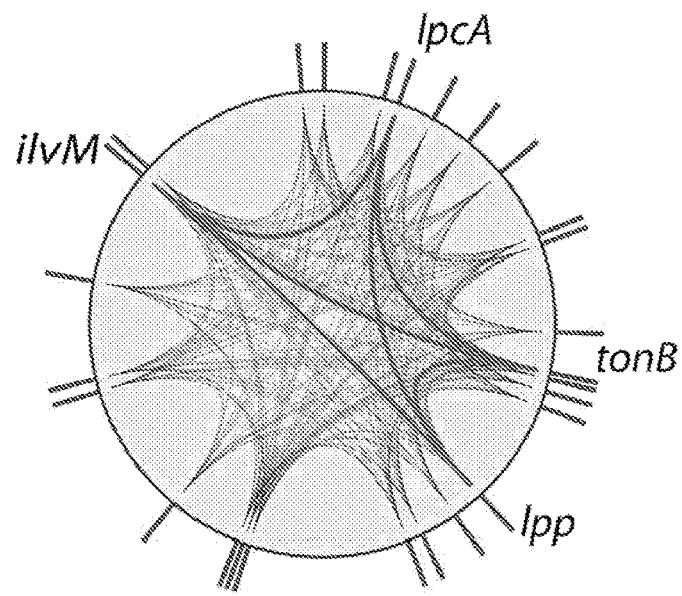
FIG. 30 is a graphical representation of all sites targeted during multiplexed recombineering are displayed on a genome map. The interactions of four genes (Ipp-IpcA-ilvM-tonB) identified to be important to hydrolysate tolerance are highlighted and studied with TRACE. These genes included proteins responsible for membrane composition (Ipp, IpcA), nucleotide biosynthesis (ilvM) and energy transduction (tonB).
Figure 31:
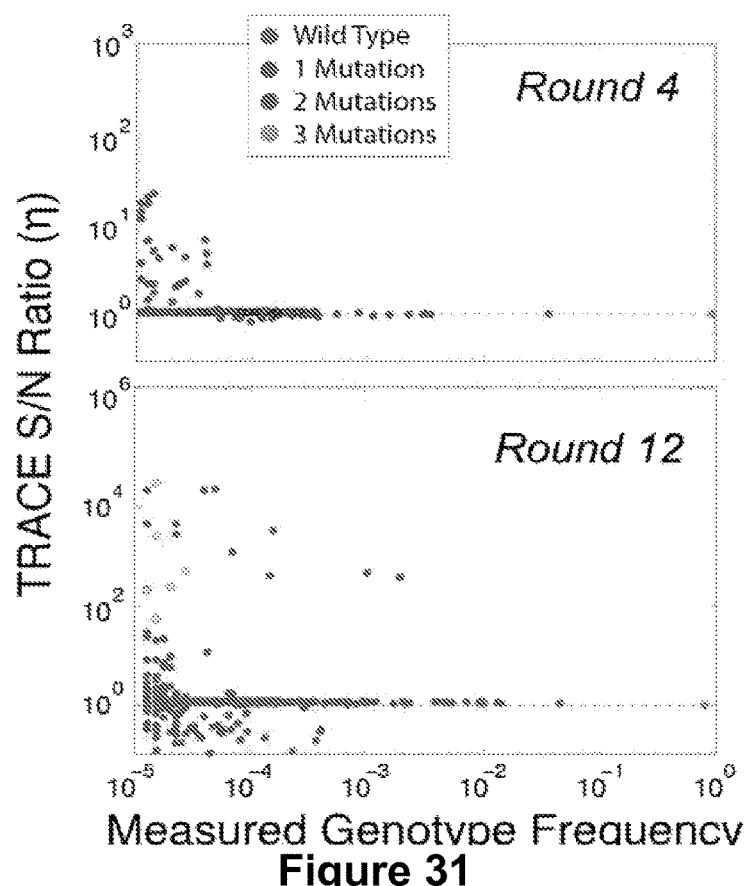
FIG. 31 shows MAGE libraries genotyped at 4 rounds of MAGE and 12 round of MAGE. The TRACE signal to noise ratio is plotted against the measured genotype frequency.

Here, the inventors employed TRACE to address this limitation by characterizing population diversity in 4 of the 27 targeted RBSs (tonB, Ipp, IpcA, ilvM) at depths 4 orders of magnitude beyond our original study (FIGS. 30 and 31). The inventors chose this particular set of 4 mutations because in prior efforts the inventors had identified mutations in the RBS of such genes. In agreement with the prior efforts, wild-type remained as the dominant member of the population. Because wild-type is so prevalent, the inventors expect the predicted crossover noise of isolated single mutants to equal the single mutation frequency:

$$f_{wt}^3 f_{mut} \sim 1; \frac{f_{mut}}{f_{wt}^3 f_{mut}} = \eta \sim 1.$$

As the number of recombineering cycles increases, the number of unique combinatorial mutants increased ~3-fold, with seven unique triple mutants observed. In the triple mutants, 18 of the 21 RBS differed from wild type by greater than 2 nucleotides, which provides clear evidence that such mutations were introduced via ssDNA recombineering. Library diversity was characterized by on samples obtained after four and twelve rounds of recursive multiplex recombineering. As expected, diversity increased with multiple rounds of recombineering. The inventors display individual genotypes as the TRACE SNR versus genotype frequency (FIG. 31), thus providing a straightforward view of both the frequency of a particular combinatorial mutant and the relative likelihood that the mutant truly exists in the population or could be explained as a crossover artifact. For further validation, the inventors compared the mutation frequency in the targeted RBS regions (a degenerate RBS design described previously) to the mutation frequency in the adjacent non-targeted regions. As expected, all mutations of greater than 5 nt were identified in the targeted RBS regions. No background mutations greater than 2 nt were observed in the non-targeted 10 nt linker regions and likely originate from low levels of sequencing error. Targeted regions included a majority of mutations between 4 to 8 nucleotides in length, in agreement with the degeneracy of the recombineering oligos used. Taken together, these data demonstrate that TRACE can provide quantitative frequency and confidence information on library diversity that does not rely upon previously employed statistical approximations.

Figures 32A, 32B:
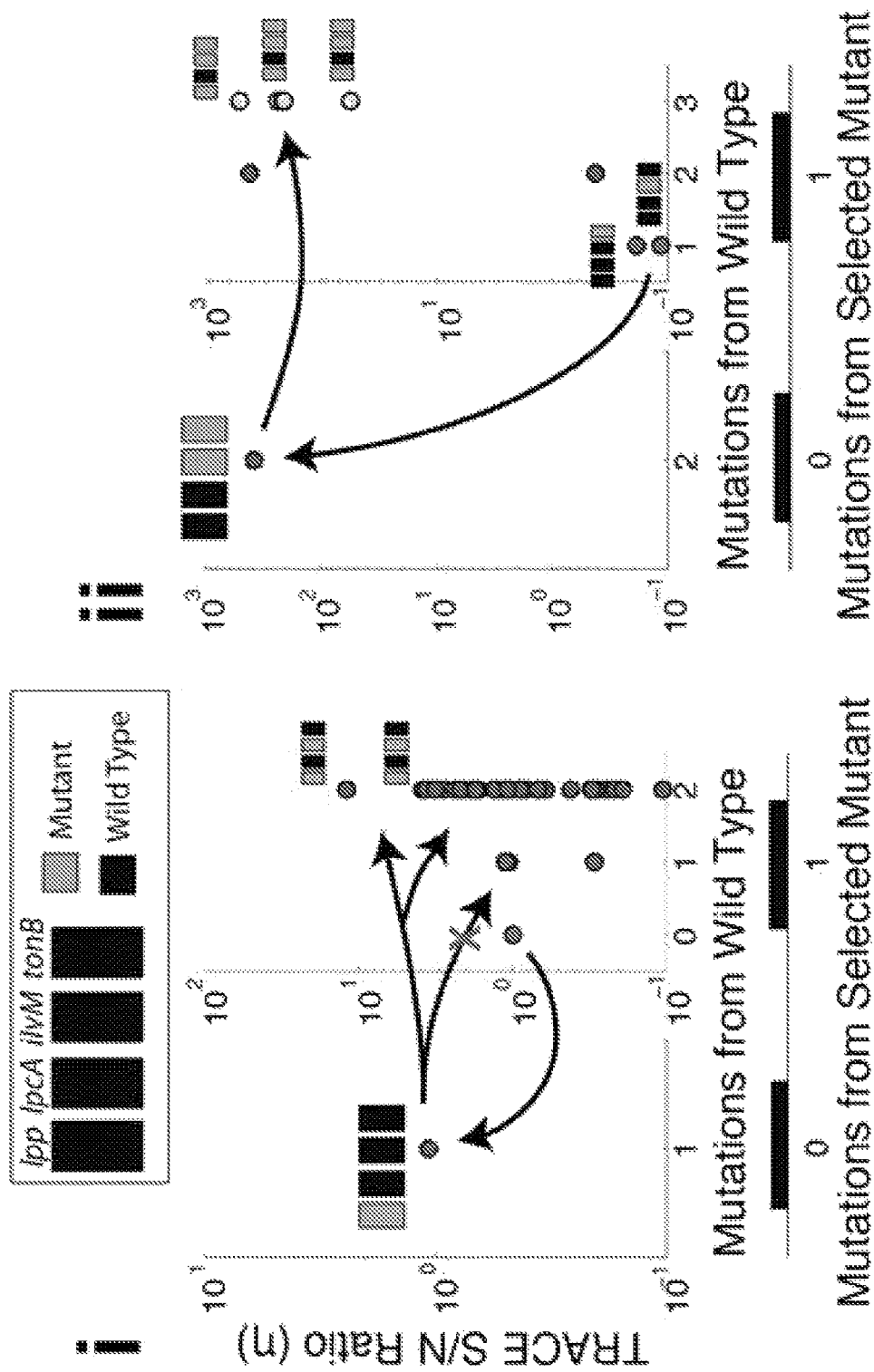
FIG. 32A shows the evolutionary trajectory of the most abundant single mutant (Ipp, 4.5%).
FIG. 32B shows the most abundant double mutant (ilvM-tong, 0.19%).

Tracking combinatorial libraries enables mapping of evolutionary trajectories of individual mutants throughout the genome engineering cycle. To demonstrate this capability, the inventors calculated the trajectories of the most abundant single (Ipp) and double (ilvM-tonB) mutants, identified at 4.5% and 0.19% frequencies, respectively, in the 12 round library (FIGS. 32A and B). The Ipp single mutant likely evolved directly from wild type, as it is highly unlikely that any single mutant is derived from anywhere but wild-type given that WT comprises over 90% of the total population. The inventors also found that the Ipp single mutant was responsible for the generation of several double mutants with differing ilvM mutations. The double mutant (ilvM-tonB) was uniquely identified to be the parent of several triple mutants (FIG. 32B). Determining the parent of this double mutant was inconclusive because both potential parents have small η(0.1 and 0.3). A possible explanation for this is that a single mutation is deleterious (dropping the actual parent from the population) while the combination of mutations is synergistic. Similar calculations could be performed for any mutant in the library at any time point of the library generation, screening, or selection process.

These studies demonstrate the application of TRACE to track and characterize changes in diversity as a result of growth selections on combinatorial libraries. The inventors specifically evaluated the combinatorial libraries described above after growth selection in medium containing 40% cellulosic hydrolysate (a growth inhibitor for *E. coli*). Under these conditions, the frequency of mutant genotypes more susceptible to hydrolysate toxicity is expected to decrease relative to more tolerant genotypes. After growth selection, the inventors observed a 50% decrease in the frequency of wild type sequences and a 30% reduction in overall diversity; demonstrating that TRACE can be used to broadly and deeply quantify selective pressure. Initial libraries contained seven triple mutants, however, only three triple mutants remained after selection, raising the possibility that negative epistasis played a role in defining the fitness of these mutants. To demonstrate the ability of TRACE to characterize epistatic interactions, the inventors compared binary coordinated gene expression (a calculated translation initiation rate) for enriched and diluted genotypes (FIG. 32B). Coordinated downregulation of both Ipp and tonB was detected for enriched genotypes. Ipp "down" mutants were identified in a previous hydrolysate selection performed in the inventors' lab. Other coordinated observations included ilvM downregulation with tonB upregulation and ilvM downregulation with wild type Ipp. This data provides insights into the types of combinatorial interactions that can be identified and evaluated using TRACE that cannot realistically by evaluated by alternative strategies.

Example 7

Figure 33:
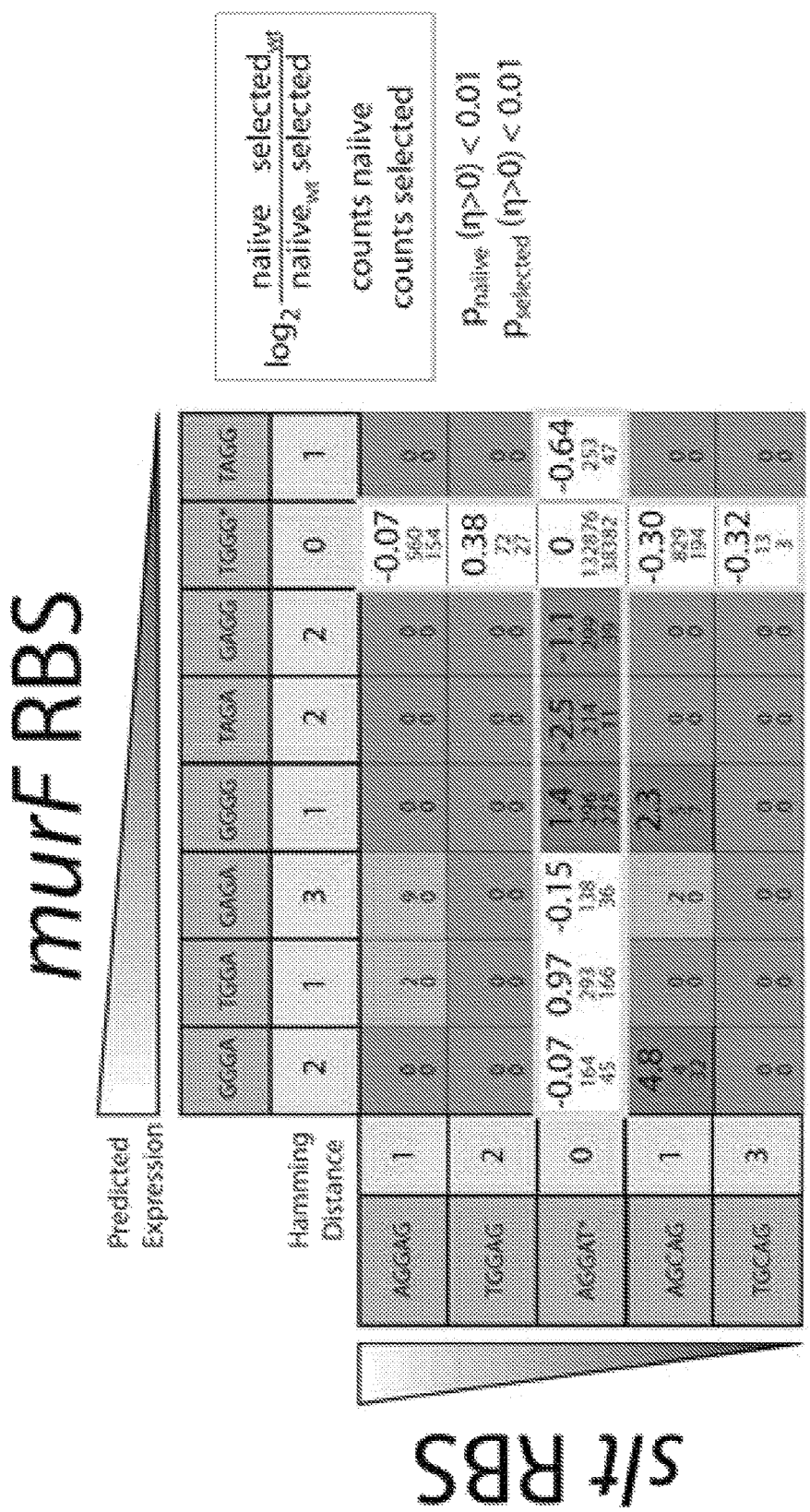
FIG. 33 shows the measured landscape of all targeted mutations between slt and murF sorted by predicted translation initiation rate. Number of counts before and after selection and relative change in frequency are included for each genotype. Single-site mutants are outlined in yellow. P-values refer to confidence that this landscape is different than a η=0 landscape generated from single site mutant frequencies.
Figure 34:
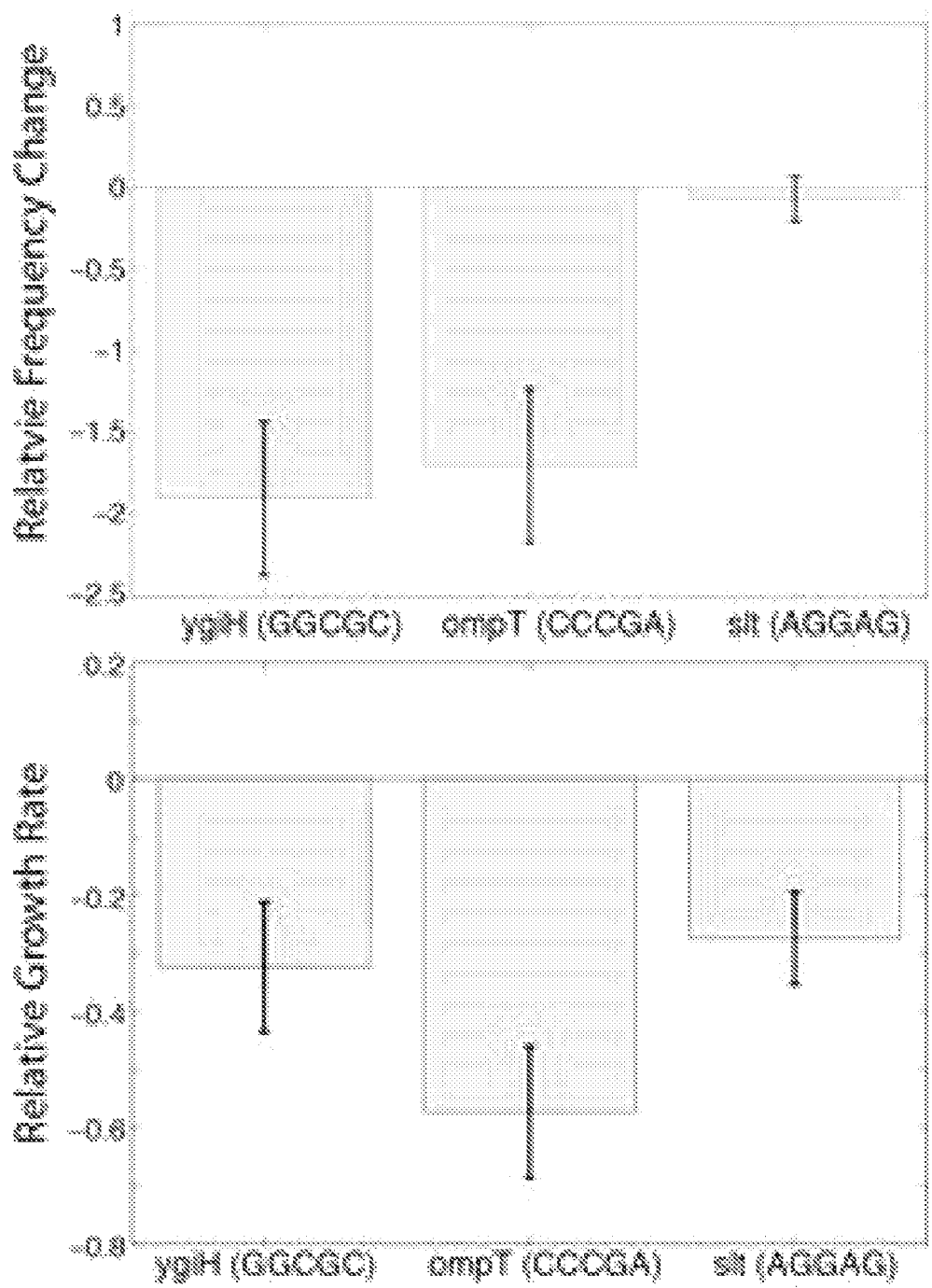
FIG. 34 shows the analysis of growth in 0.75% isobutanol for three strains enriched via colony TRACE sequencing and three sites independently generated from MAGE having slt-murF mutations.

To provide another real-world yet orthogonal validation of TRACE, the inventors engineered a new combinatorial library by 12 rounds of multiplex recombineering targeting the RBS of six genes previously identified to influence alcohol tolerance. To provide a higher dynamic range for expression, degenerate RBS sequences were custom-designed for each gene based on minimizing degeneracy while maximizing expression range. Library diversity was characterized by TRACE before and after isobutanol selections. First, the inventors validated the reproducibility of TRACE data by performing three technical replicates ($R^2$=0.9997). This data reinforces the conclusions drawn in the earlier Examples in this disclosure regarding the ability of TRACE to provide quantitative and accurate data on library diversity. The majority of individual and combinatorial mutants identified in the population had reduced fitness. However, individual mutants with improved fitness were identified for all targeted genes except ompT. Moreover, two double mutants (murF upregulated and slt downregulated) with improved fitness were also identified. The validity of this interaction was further explored by examining the fitness landscape of all 28 possible double-mutants between murF and slt (FIG. 33). Approximately 130,000 reads contained wild-type RBS sequences for both murF and slt, and ~3,000 reads contained one of the eleven mutant RBS sequences in front of murF or slt. All 11 designed RBS sequences were identified, and ~22 reads contained RBS mutations in both murF and slt, with a total of five unique double mutant genotypes identified. The fact that the inventors identified a low level of combinatorial mutants reinforces the lack of any substantial crossover during TRACE assembly, where in a scenario of high crossover a much larger level of double mutants should have been identified given the relatively high number of single mutants identified. To further validate the TRACE emulsion based results, Sanger sequencing of 40 TRACE six-site assemblies from individual colonies (240 sites in 40 individual reactions) was performed. High-throughput emulsion-based sequencing and colony-based sequencing results were in agreement—specifically, three single mutants (3 of 39 successful TRACE assemblies) were identified via Sanger sequencing, whereas the high-throughput results predict about 10% mutant genotypes. All mutant colony TRACE genotypes identified were also present in the high-throughput TRACE data. In addition, each of the three single mutants was measured by TRACE to have a negative fitness in the isobutanol selections, a result that was subsequently validated by separate individual growth measurements (FIG. 34).

TRACE presents an opportunity to shift from identifying single mutations in populations to quantitatively mapping more complex genotypes generated by targeted combinatorial genome-editing methods. Here, individual strains containing mutations in up to ten sites, several combinatorial libraries generated by recursive multiplex recombineering, and combinatorial interactions affecting fitness were evaluated with TRACE. TRACE is currently limited by sequencing read lengths (<1 kb), yet should be scalable with advances in the read-length of higher-throughput sequencing technologies, thus enabling the population-wide tracking of increasingly complex designs (although multiple TRACE assemblies could be evaluated in parallel currently). Although several additional large assemblies have been constructed of 8-10 sites and constructs of >10 sites are shown to be kinetically favorable, the current size limit of construction is unknown but likely dictated by sequence complexity and primer design stringency. Even though small levels of crossover were observed, the inventors provide a mechanism for rapidly assigning confidence to any identified mutant (TRACE S/N) and emphasize that high-throughput microwell technology or more uniform emulsion generation with proven microfluidic techniques can be employed to reduce crossover noise and improve genotype identification and quantification. While TRACE was demonstrated primarily on different multiplexed recombineering *E. coli* libraries, given the generality of PCR, emulsion, and sequencing technologies, the approach will work on broad range of model organisms, as demonstrated in this disclosure for the ES2 human ovarian carcinoma cancer cell line. Although, recombineering efficiencies were low, but consistent between two libraries tested, additional recombineering cycles can be performed assisted by previously reported recursive automation technologies. In addition to demonstrated genome-based combinatorial optimization, TRACE can be applied to track metabolic changes using different synthetic approaches that regulate metabolic processes using small-regulatory RNAs, CRISPR regulation and barcoded synthetic constructs. TRACE matches the throughput of library construction and evaluation efforts, which thereby enables a fully integrated engineering cycle where combinatorial design rules can be more quickly ascertained and leveraged in recursive engineering and optimization efforts.

The foregoing examples of the present invention have been presented for purposes of illustration and description. Furthermore, these examples are not intended to limit the invention to the form disclosed herein. Consequently, variations and modifications commensurate with the teachings of the description of the invention, and the skill or knowledge of the relevant art, are within the scope of the present invention. The specific embodiments described in the examples provided herein are intended to further explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. A method to assemble target sequences within a heterogenous population of nucleic acid molecules in a one pot reaction comprising:
    a) amplifying a sample of heterogenous nucleic acid molecules containing at least three target sequences in non-adjacent portions of target DNA in a composition comprising at least three amplification primer pairs, to form a contiguous nucleic acid product molecule comprising each of the at least three target sequences,
        wherein each of the at least three amplification primer pairs specifically amplifies one of the target sequences; and,
        wherein at least one amplification primer from each of the at least three amplification primer pairs comprises a linker sequence that is complementary to, and hybridizes with, a sequence internal to a DNA segment from another one of the at least three amplification primer pairs; and,
    b) amplifying the contiguous nucleic acid product molecule in a composition comprising one amplification primer pair to form multiple copies of the contiguous nucleic acid product molecule.

2. The method of claim 1, wherein the amplifying steps a) and b) are polymerase chain reaction PCR amplification reactions comprising a DNA polymerase, and deoxyribonucleoside triphosphates (dNTPs).

3. The method of claim 2, wherein the polymerase is selected from the group consisting of *Thermus thermophilus* (Tth) DNA polymerase, *Thermus aquaticus* (Taq) DNA polymerase, *Thermotoga neopolitana* (Tne) DNA polymerase, *Thermotoga maritima* (Tma) DNA polymerase, *Thermococcus litoralis* (Tli or VENT™) DNA polymerase, *Pyrococcus furiosus* (Pfu or DEEPVENT™) DNA polymerase, *Pyrococcus woosii* (Pwo) DNA polymerase, *Bacillus sterothermophilus* (Bst) DNA polymerase, *Sulfolobus acidocaldarius* (SAC) DNA polymerase, *Thermoplasma acidophilum* (Tac) DNA polymerase, *Thermus flavus* (Tfl/Tub) DNA polymerase, *Thermus ruber* (Tru) DNA polymerase, *Thermus brockianus* (DYNAZYIVIIE™) DNA polymerase, *Methanobacterium thermoautotrophicum* (Mth) DNA polymerase, and mutants, variants, and derivatives thereof.

4. The method of claim 2, wherein the amplifying step a) comprises an excess of dNTPs proportional to the number of sites assembled.

5. The method of claim 1, wherein the amplifying steps a) and b) are polymerase chain reaction (PCR) amplification reactions conducted under conditions suitable for denaturing the nucleic acid molecules, and then annealing of the linker sequence present on one amplification primer to the linker sequence present on one amplification primer from another amplification primer pair.

6. The method of claim 1, wherein each of the linker sequences are 29 nucleotides in length.

7. The method of claim 1, wherein each of the linker sequences are independently at least 24 nucleotides in length and have a melting temperature of at least 60° C.

8. The method of claim 1, wherein each of the amplification primer sequences are between 18 and 30 nucleotides in length.

9. The method of claim 1, wherein each of the amplifying steps are conducted for 35 cycles.

10. The method of claim 1, wherein the amplifying step a) is conducted in a single reaction vessel.

11. The method of claim 1, wherein each of the amplifying steps a) and b) are conducted in a separate reaction vessel.

12. The method of claim 1, further comprising: sequencing the contiguous nucleic acid molecule to identify at least one mutation present in a target sequence.

13. The method of claim 1, wherein each of the linker sequences are independently at least 24 nucleotides in length.

* * * * *